United States Patent
Nilson et al.

(10) Patent No.: US 7,474,399 B2
(45) Date of Patent: Jan. 6, 2009

(54) DUAL ILLUMINATION SYSTEM FOR AN IMAGING APPARATUS AND METHOD

(75) Inventors: David Nilson, Walnut Creek, CA (US); Brad Rice, Danville, CA (US); Tamara Troy, San Francisco, CA (US)

(73) Assignee: Xenogen Corporation, Alameda, CA (US)

( * ) Notice: Subject to any disclaimer, the term of this patent is extended or adjusted under 35 U.S.C. 154(b) by 335 days.

(21) Appl. No.: 11/434,606

(22) Filed: May 15, 2006

(65) Prior Publication Data

US 2006/0203244 A1   Sep. 14, 2006

(51) Int. Cl.
*G01N 21/00* (2006.01)
*G01J 3/30* (2006.01)
*G01K 9/00* (2006.01)

(52) U.S. Cl. .................. 356/317; 382/154; 600/309; 356/73

(58) Field of Classification Search .................. 356/317, 356/318, 417, 73; 382/154, 110; 600/309
See application file for complete search history.

(56) References Cited

U.S. PATENT DOCUMENTS

| | | | |
|---|---|---|---|
| 3,871,767 A | 3/1975 | Holm-Hansen et al. |
| 4,076,420 A | 2/1978 | De Maeyer et al. |
| 4,582,406 A | 4/1986 | Wally |
| 4,593,728 A | 6/1986 | Whitehead et al. |
| 4,708,475 A | 11/1987 | Watson |
| 4,863,690 A | 9/1989 | Berthold et al. |
| 5,039,868 A | 8/1991 | Kobayashi et al. |
| 5,202,091 A | 4/1993 | Lisenbee |
| 5,319,209 A | 6/1994 | Miyakawa et al. |
| 5,414,258 A | 5/1995 | Liang |
| 5,542,012 A | 7/1996 | Fernandes et al. |
| 5,636,299 A | 6/1997 | Bueno et al. |
| 5,637,874 A | 6/1997 | Hammanatsu |

(Continued)

FOREIGN PATENT DOCUMENTS

EP  0493707  3/1996

(Continued)

OTHER PUBLICATIONS

Partial Search Report dated Dec. 17, 2007 in PCT Application No. PCT/US2007/011643.

(Continued)

*Primary Examiner*—L. G Lauchman
(74) *Attorney, Agent, or Firm*—Beyer Law Group LLP

(57) ABSTRACT

A dual illumination system is disclosed for use with an imaging apparatus. The imaging apparatus defines a light-tight imaging compartment with an interior wall having a view port extending into the imaging compartment. This view port enables data acquisition of a biological specimen contained in the imaging compartment. The dual illumination system includes a first illumination assembly configured to direct structured light onto a first side of the specimen to enable structured light and surface topography measurements thereof. A second illumination assembly then directs light at the specimen wherein diffused fluorescent light emanates from a surface thereof for receipt through the view port to acquire fluorescence data of the specimen. The combination of structured light imaging and fluorescence imaging enables 3D diffuse tomographic reconstructions of fluorescent probe location and concentration.

32 Claims, 24 Drawing Sheets

U.S. PATENT DOCUMENTS

| | | |
|---|---|---|
| 5,650,135 A | 7/1997 | Contag et al. |
| 5,672,881 A | 9/1997 | Striepeke et al. |
| 5,680,492 A | 10/1997 | Hopler et al. |
| 5,705,807 A | 1/1998 | Throngnumchai |
| 5,738,101 A | 4/1998 | Sappey |
| 5,840,572 A | 11/1998 | Copeland et al. |
| 5,867,250 A | 2/1999 | Baron |
| 5,898,802 A | 4/1999 | Chen et al. |
| 5,916,160 A | 6/1999 | Arcan et al. |
| 5,943,129 A | 8/1999 | Hoyt et al. |
| 5,970,164 A | 10/1999 | Bamberger |
| 5,986,271 A | 11/1999 | Lazarev et al. |
| 6,036,920 A | 3/2000 | Pantoliano et al. |
| 6,043,506 A | 3/2000 | Heffelfinger et al. |
| 6,071,748 A | 6/2000 | Modlin et al. |
| 6,084,680 A | 7/2000 | Tuunanen et al. |
| 6,097,025 A | 8/2000 | Modlin et al. |
| 6,217,847 B1 | 4/2001 | Contag et al. |
| 6,242,743 B1 | 6/2001 | DeVito et al. |
| 6,321,111 B1 | 11/2001 | Perelman et al. |
| 6,364,829 B1 | 4/2002 | Fulghum |
| 6,373,568 B1 | 4/2002 | Miller et al. |
| 6,381,058 B2 | 4/2002 | Ramm et al. |
| 6,403,947 B1 | 6/2002 | Hoyt et al. |
| 6,510,281 B2 | 1/2003 | Schroder |
| 6,597,864 B2 | 7/2003 | Schroder |
| 6,615,063 B1 | 9/2003 | Ntziachristos |
| 6,665,072 B2 | 12/2003 | Hoyt |
| 6,690,466 B2 | 2/2004 | Miller et al. |
| 6,693,710 B1 | 2/2004 | Hoyt |
| 6,750,964 B2 | 6/2004 | Levenson et al. |
| 6,775,567 B2 | 8/2004 | Cable et al. |
| 6,894,289 B2 | 5/2005 | Nilson et al. |
| 6,901,279 B2 | 5/2005 | Cable et al. |
| 6,922,246 B2 | 7/2005 | Nilson et al. |
| 6,924,893 B2 | 8/2005 | Oldenbourg et al. |
| 7,177,024 B2 | 2/2007 | Nilson et al. |
| 2001/0028510 A1 | 10/2001 | Ramm et al. |
| 2005/0201614 A1 | 9/2005 | Rice et al. |
| 2005/0237423 A1 | 10/2005 | Nilson et al. |

FOREIGN PATENT DOCUMENTS

| | | |
|---|---|---|
| EP | 0718622 | 5/2003 |
| WO | WO 99/08233 | 2/1999 |
| WO | WO00/17643 | 3/2000 |
| WO | WO 00/49938 | 8/2000 |
| WO | WO00/50872 | 8/2000 |
| WO | WO 01/61324 | 8/2001 |
| WO | WO 01/63247 | 8/2001 |
| WO | WO 03/073079 | 9/2003 |
| WO | WO 2005/089637 | 9/2005 |

OTHER PUBLICATIONS

Yang, Meng. et al., *Visualizing gene expression by whole-body fluorescence imaging*, PNAS, 12278-12282, Oct. 24, 2000, vol. 97, No. 22.

Reichman, Jay, *Handbook of Optical Filters For Fluorescence Microscopy*, Chroma Technology Corp. HB1.1, Jun. 2000.

Yang, Meng, et al., *Whole-body optical imaging of green fluorescent protein-expressing tumors and metastases*, PNAS, 1206-1211, Feb. 1, 2000, vol. 97, No. 3.

PCT patent application No. PCT/US03/05199, International Search Report dated Dec. 10, 2003.

PCT patent application No. PCT/US03/05199, Preliminary Examination Report dated Dec. 10, 2003.

European Patent Application No. 03 713 577.9-2204, Examination report dated Feb. 20, 2006.

Hamamatsu Corporation, USA, website. http://usa.hamamatsu.com/ pp. 1-4, Apr. 27, 2001, printed on Apr. 27, 2001.

VetEquip Incorporated website, http://www.vetequip.com/1806.htm Table Top Laboratory Animal Anesthesia System, Apr. 27, 2001, printed on Apr. 27, 2001.

VetEquip Incorporated website, http://www.vetequip.com/1807.htm Mobile Laboratory Animal Anesthesia System, Apr. 27, 2001, printed on Apr. 27, 2001.

Hamamatsu, Imaging Box Instruction Manual, 55310-224-1, Nov. 2000.

Vet Equip Incorporated website, http://www.vetequip.com/impac. htm IMPAC$_6$ An anesthesia system designed for high volume, assembly-line type procedures, Apr. 27, 2001, printed on Apr. 27, 2001.

PCT/US01/06078, International Preliminary Exam Report mailed Dec. 9, 2002.

PCT/US01/06078, International Search Report mailed Feb. 23, 2001.

PCT/US01/06078, Written Opinion mailed Jun. 14, 2002.

Mahmood, et al., *Near-Infrared Optical Imaging of Protease Activity for Tumor Detection*, Radiology, Dec. 1999, pp. 866-870.

Weissleder, et al., *Shedding Light onto Live Molecular Targets*, Nature Medicine, vol. 9, No. 1, Jan. 2003, pp. 123-128.

Australia application No. 2001241758, Examiner's First Report dated Nov. 18, 2004.

Office Action dated Mar. 17, 2008 from U.S. Appl. No. 11/670,376.

International Search Report dated Apr. 9, 2008 from PCT Application No. PCT/US2007/011643.

Written Opinion dated Apr. 9, 2008 from PCT Application No. PCT/US2007/011643.

Notice of Allowance dated Jul. 29, 2008 from U.S. Appl. No. 11/670,376.

Notice of Allowance dated Oct. 17, 2008 from U.S. Appl. No. 11/434,605.

DUAL ILLUMINATION SYSTEM FOR AN IMAGING APPARATUS AND METHOD

CROSS-REFERENCE TO RELATED APPLICATION

This application is related to U.S. patent application entitled "BOTTOM FLUORESCENCE ILLUMINATION ASSEMBLY FOR AN IMAGING APPARATUS" by Nilson et al., filed Jun. 17, 2005, U.S. application Ser. No. 11/155,078; which in turn is a continuation of a U.S. patent application entitled "BOTTOM FLUORESCENCE ILLUMINATION ASSEMBLY FOR AN IMAGING APPARATUS" by Nilson et al., filed Feb. 21, 2003, U.S. application Ser. No. 10/372,763, which in turn is a continuation-in-part of a U.S. patent application entitled "FLUORESCENCE ILLUMINATION ASSEMBLY FOR AN IMAGING APPARATUS" by Nilson et al., filed Jul. 3, 2002, U.S. application Ser. No. 10/189,886, now issued as U.S. Pat. No. 6,894,289, which in turn claims priority under 35 U.S.C. 119(e) from U.S. Provisional Patent Application No. 60/359,663, entitled same and filed Feb. 22, 2002; all are incorporated herein by reference for all purposes.

TECHNICAL FIELD

The present invention relates generally to optical imaging systems, and more particularly, relates to fluorescent illumination sources and their associated components to illuminate targeted fluorescent probes in tissue.

BACKGROUND

One specialized type of imaging involves the capture of low intensity fluorescence from animal subjects such as mice. Briefly, fluorescence is a molecular phenomenon in which a substance absorbs light of a particular wavelength and emits light of a longer wavelength. The absorption of light is referred to as the "excitation", and the emission of longer wave lights as the "emission". Both organic and inorganic substances can exhibit fluorescent properties.

Fluorescence imaging is performed by illuminating a sample to excite fluorescence molecules in the sample, and then capturing an image of the sample as it fluoresces using a camera. Such imaging applications present particular challenges to the design of a box or chamber in which the sample is contained during imaging. This is especially true in macroscopic applications where the field-of-view is about 1 cm–30 cm in diameter, as compared to microscopic applications where the field-of-view is less than about 1 cm.

Typically, intensified or cooled charge-coupled device (CCD) cameras are used to detect the fluorescence of low intensity light radiating from the sample. These cameras are generally complex, may require specialized cooling, and are typically fixed to a single location on the top of a specimen chamber. A user places a sample at a predetermined position in the specimen chamber within the field of view for the overhead camera.

Due to this static design, one particular challenge to imaging apparatus design is the diverse fluorescent illumination needs required during image capture. Fluorescent image capture, of course, involves the sample being illuminated with an illumination source, while the minute amounts of light emitted from the "excited" sample are detected using a light detector, e.g., a CCD camera. Depending on the application, there are benefits to both epi-illumination (reflection) and trans-illumination for fluorescence imaging. Epi-illumination provides a faster survey of the entire animal, but is subject to higher levels of autofluorescence. Trans-illumination, on the other hand, provides lower levels of autofluorescence and is useful for performing 3D tomographic reconstructions. Therefore, it is desirable to have both epi- and trans-illumination options on a fluorescence imaging system.

It is also desirable to determine the 3D location and concentration of fluorescent probes in tissue. Diffuse tomographic reconstruction algorithms are often used for this purpose. To perform 3D diffuse tomographic reconstructions in fluorescence imaging, however, it is necessary to determine a 3D surface topography of the target specimen. The surface topography is used to define the boundary conditions within the diffuse tomography algorithm. One particularly suitable technique to determine the 3D surface topography of a specimen is through the application of structured light imaging. It would be desirable to provide a single imaging system that is capable of both structured light imaging, to obtain 3D surface topography, and fluorescent imaging, to perform 3D diffuse tomographic reconstructions of a specimen. The present invention describes a dual illumination system that accomplishes these objectives.

DISCLOSURE OF INVENTION

The present invention provides a dual illumination system for use with an imaging apparatus. The imaging apparatus defines a light-tight imaging compartment with an interior wall having a view port extending into the imaging compartment. This view port enables data acquisition of a biological specimen contained in the imaging compartment. The dual illumination system includes a first illumination assembly configured to direct structured light imaging onto a first side of the specimen to enable structured light and surface topography measurements thereof. A second illumination assembly then directs excitation light at the specimen wherein diffused fluorescent light emanates from a surface thereof for receipt through the view port to acquire fluorescence data of the specimen.

Accordingly, a single imaging apparatus is provided that utilizes a dual illumination system capable of both structure light imaging and diffused fluorescent excitation light imaging. Hence, the structured light imaging is applied to determine the 3D surface tomography of the specimen, while the fluorescent excitation light imaging is applied to determine the fluorescence imaging data. Using this collection of data, 3D diffuse fluorescence tomographic reconstructions In one specific embodiment, the second illumination assembly includes one of a trans-illumination device and an epi-illumination device. The trans-illumination device is configured to direct light into a first surface of the specimen wherein the diffused light exits a second surface thereof for receipt through the view port. The epi-illumination device is configured direct light onto a third surface of the specimen wherein the diffused light exits the third surface thereof for receipt through the view port.

More particularly, the trans-illumination device is configured to direct light into a bottom surface of the specimen wherein the diffused light exits a topside surface thereof for receipt through the of the diffused light from the view port. Further, the epi-illumination device is configured direct light onto the topside surface of the specimen wherein the diffused light exits the topside surface thereof for receipt through the view port.

In another configuration, the epi-illumination device includes a first light transmission unit having a proximal end thereof in optical communication with an excitation light source and a distal end thereof terminating proximate the view port. The trans-illumination device includes a second light transmission unit having a respective proximal end thereof in optical communication with the excitation light source and a respective distal end thereof configured to direct the light into the bottom side surface of the specimen.

The trans-illumination device includes an illumination output device configured to cooperate with the distal end of second light transmission unit to emit a pinpoint beam of the light toward a window portion of a support platform in the compartment. The trans-illumination device further includes a translation mechanism supporting the illumination output device to selectively position the pinpoint beam of light at one of a plurality of positions adjacent the window portion.

In yet another specific embodiment, the epi-illumination device includes an illumination output end disposed directly into the imaging compartment, and positioned proximate to and peripherally encircling the view port such that the specimen platform is illuminated in a substantially uniform manner. The epi-illumination device includes a frame substantially peripherally encircling the view port, and adapted to support the output end of the illumination device. The epi-illumination device includes a bundle of fiber optic strands extending into the imaging compartment at the output end. The fiber optic strands have respective distal ends thereof terminating at the frame to emit a conical directional beam of light onto the specimen platform. The distal ends of the fiber optic strands being sufficiently spaced peripherally about the view port such that the plurality of directional beams collectively illuminate the specimen platform in the substantially uniform manner.

Another particular arrangement provides a first illumination assembly that includes a laser galvanometer device.

In another specific embodiment, the second illumination assembly includes an optical light switch positioned between an excitation light sources and the proximal ends of the respective first and second light transmission units. This optical light switch is configured to selectively direct the excitation light to one of the epi-illumination device and the trans-illumination device.

In particular, the light switch includes a housing defining an interior cavity. A proximal end of the first light transmission unit optically communicates with the cavity along a first light path. Further, a proximal end of a second light transmission unit optically communicates with the cavity along a second light path, while a distal end of a third light transmission unit optically communicates with the cavity along a third light path. The light switch further includes an optical switch element that is selectively movable between a first position and a second position. In the first position, substantially all of a light passing through the third light transmission unit from the distal end thereof enters the proximal end of the first light transmission unit, while in the in the second position, substantially all of a light passing through the third light transmission unit from the distal end thereof enters the proximal end of the second light transmission unit.

In one specific arrangement, the first light path is in substantially linear, co-axial alignment with the third light path, and the second light path is in non-linear alignment with the third light path. Further, the switch element, in the first position, is positioned out of the optical path of the light transmitted in substantially linear, co-axial alignment substantially along the third light path to substantially along the first light path. In the second position, the switch element is positioned in the optical path of the light transmitted along the third light path and configured to optically redirect the light substantially in the direction the second light path and into the proximal end of the second light transmission unit. In particular, the switch element includes reflective element configured to reflect the excitation light in the direction from the third light path to the second light path, in the second position.

In yet another specific embodiment, the second light path is oriented substantially perpendicular to the first light path and the third light path. Further, the first light path, the second light path and the third light path are contained in substantially the same plane.

The switch element includes a cover device configured to cooperate with the proximal end of the second light transmission unit, in the first position, to substantially block the passage of light into the proximal end of the second light transmission unit from the housing cavity. The cover device further includes an aperture extending therethrough. When the switch element is oriented in the second position, the aperture is co-axially aligned with the second light path to enable the passage of the redirected light through the cover device and into the proximal end of the second light transmission unit.

In still another aspect of the present invention, a method is provided for performing 3D diffuse fluorescence tomography reconstruction in a single imaging apparatus. The method includes applying structured light to a surface of the specimen in the imaging compartment to determine the 3D surface topography thereof, and applying fluorescence excitation light to the specimen to acquire fluorescence imaging data thereof. The fluorescence excitation light may be directed toward the specimen in epi-illumination (reflection) mode or trans-illumination mode. The method further includes calculating the 3D diffuse fluorescence tomography reconstruction using the 3D surface topography data where the 3D surface topography obtained from structured light images acquired within the single imaging apparatus.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

BEST MODE OF CARRYING OUT THE INVENTION

Figure 1:
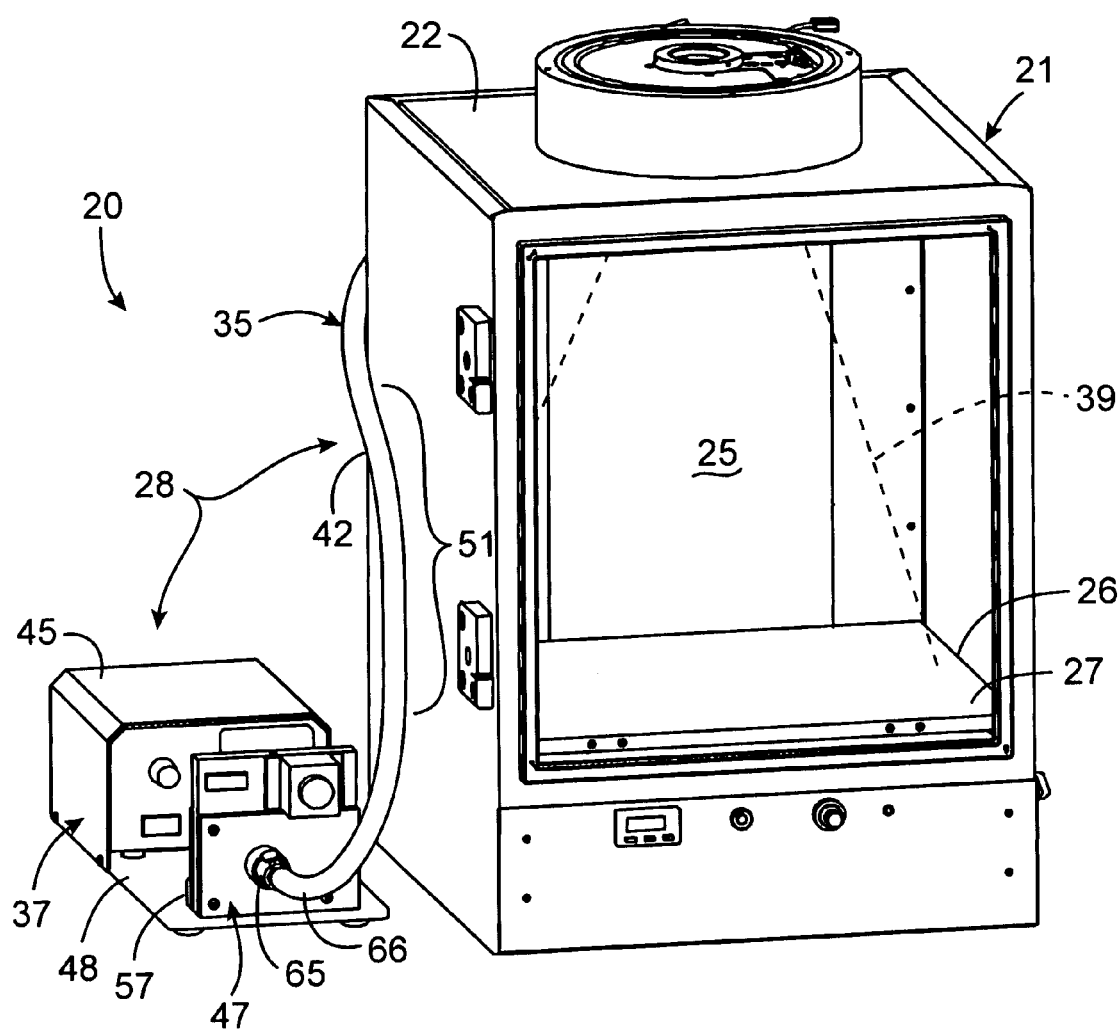
FIG. 1 is a top perspective view of an imaging apparatus, with the door removed, incorporating an illumination assembly constructed in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 9:
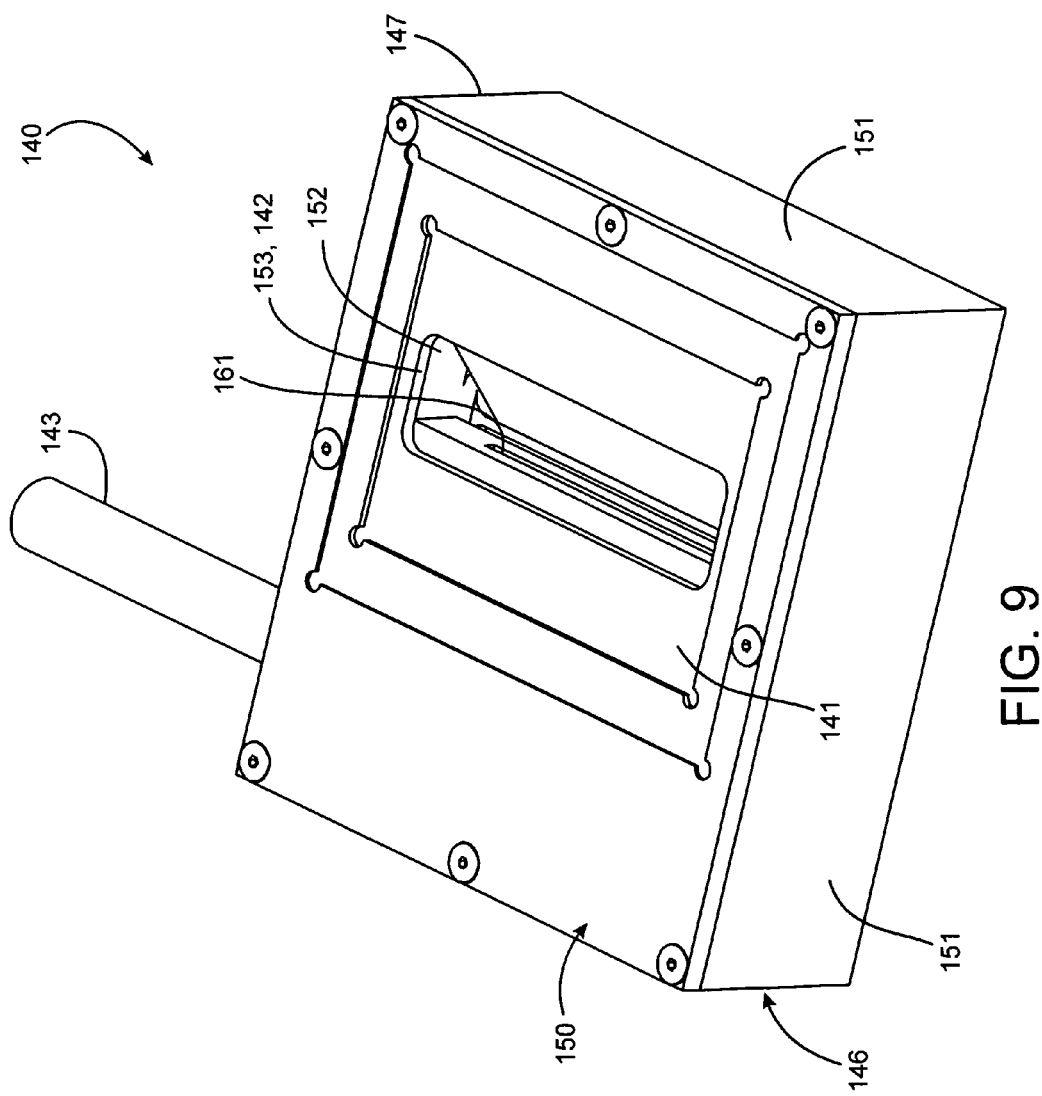
FIG. 9 is an enlarged, top perspective view of the bottom illumination assembly of FIG. 8 without the specimen thereatop.
Figure 10:
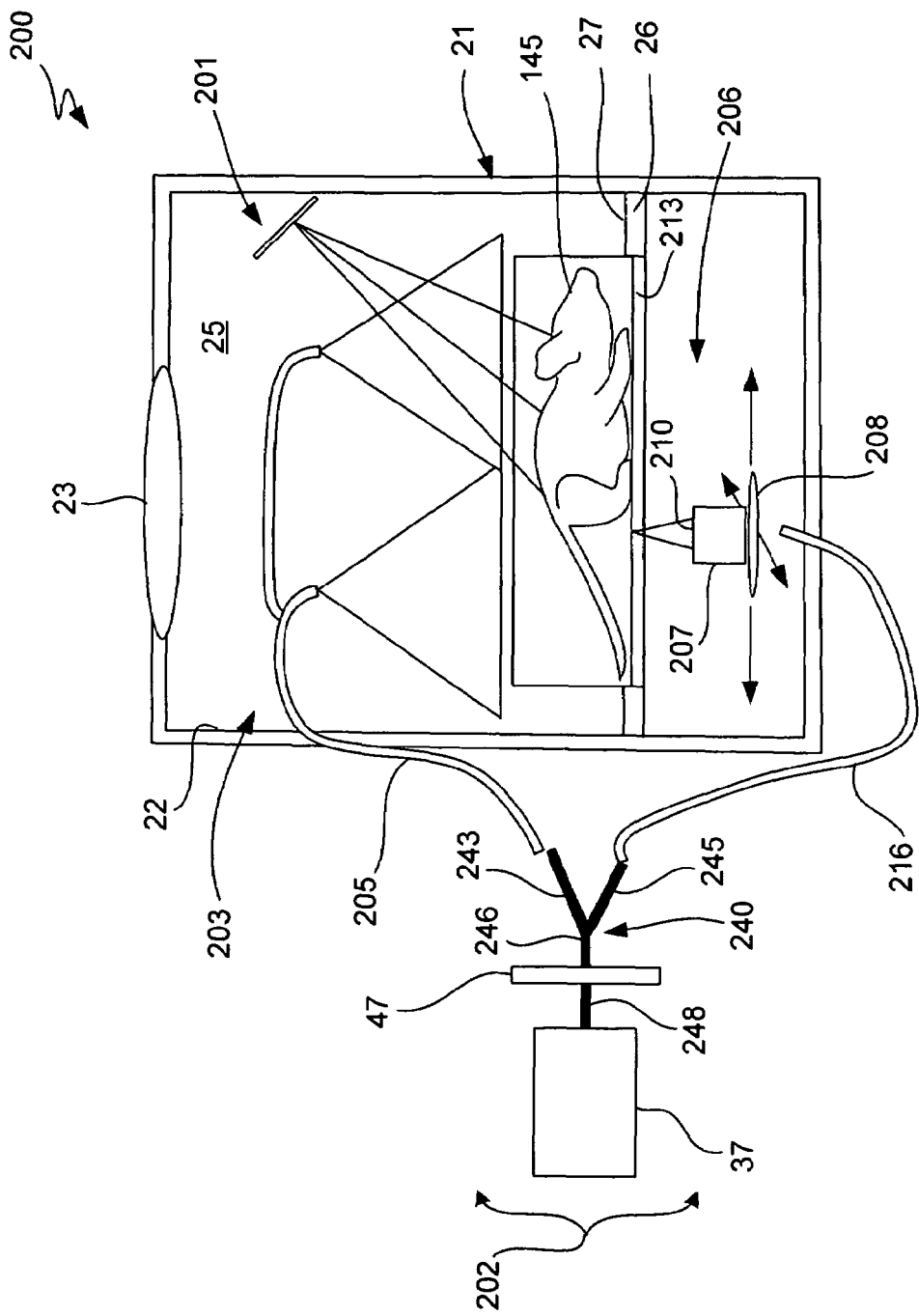
FIG. 10 is a schematic view of a dual illumination system constructed in accordance with the present invention.
Figure 11:
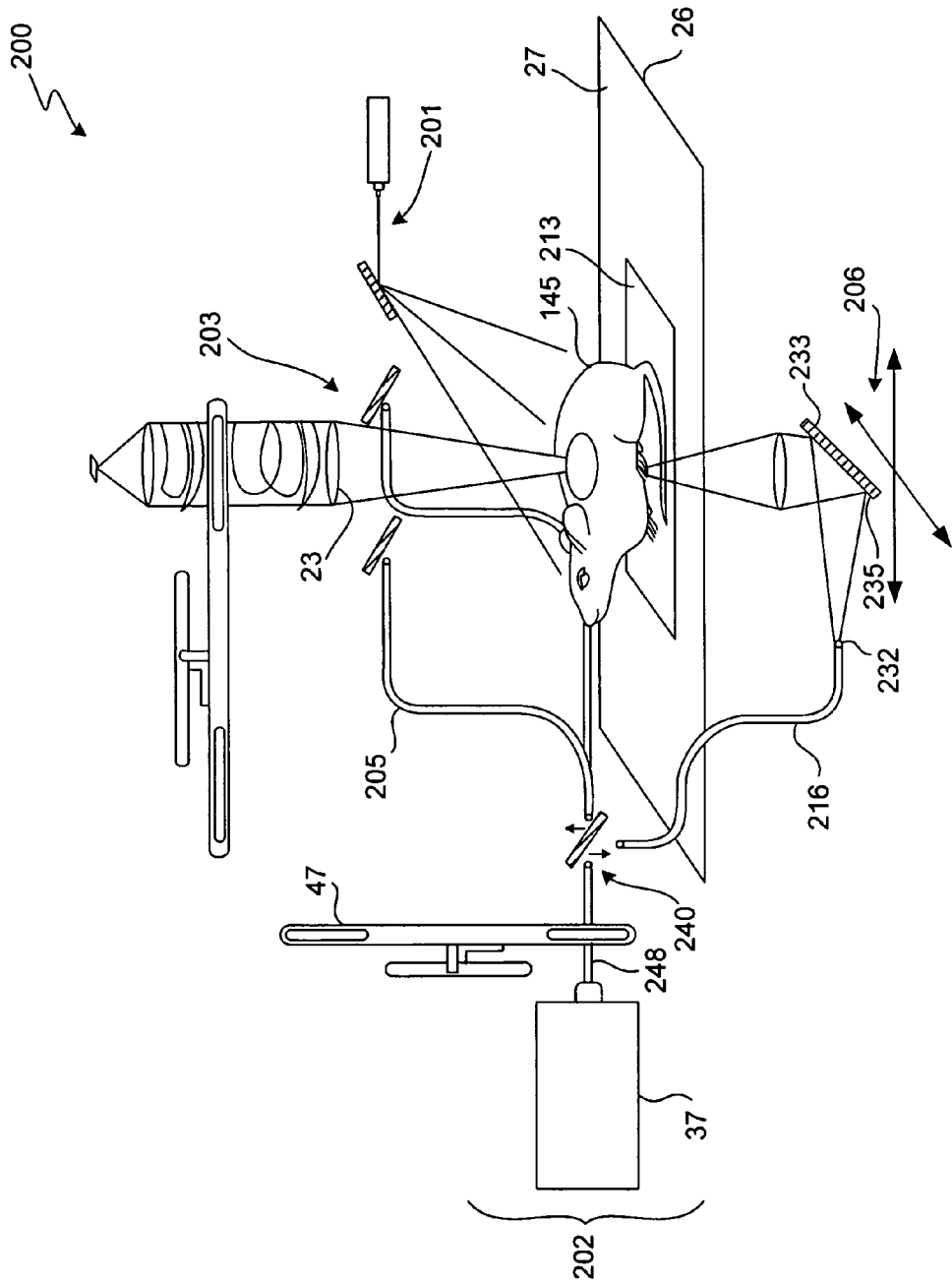
FIG. 11 is a schematic view of the dual illumination system of FIG. 10 with an alternative embodiment trans-illumination device.
Figure 12:
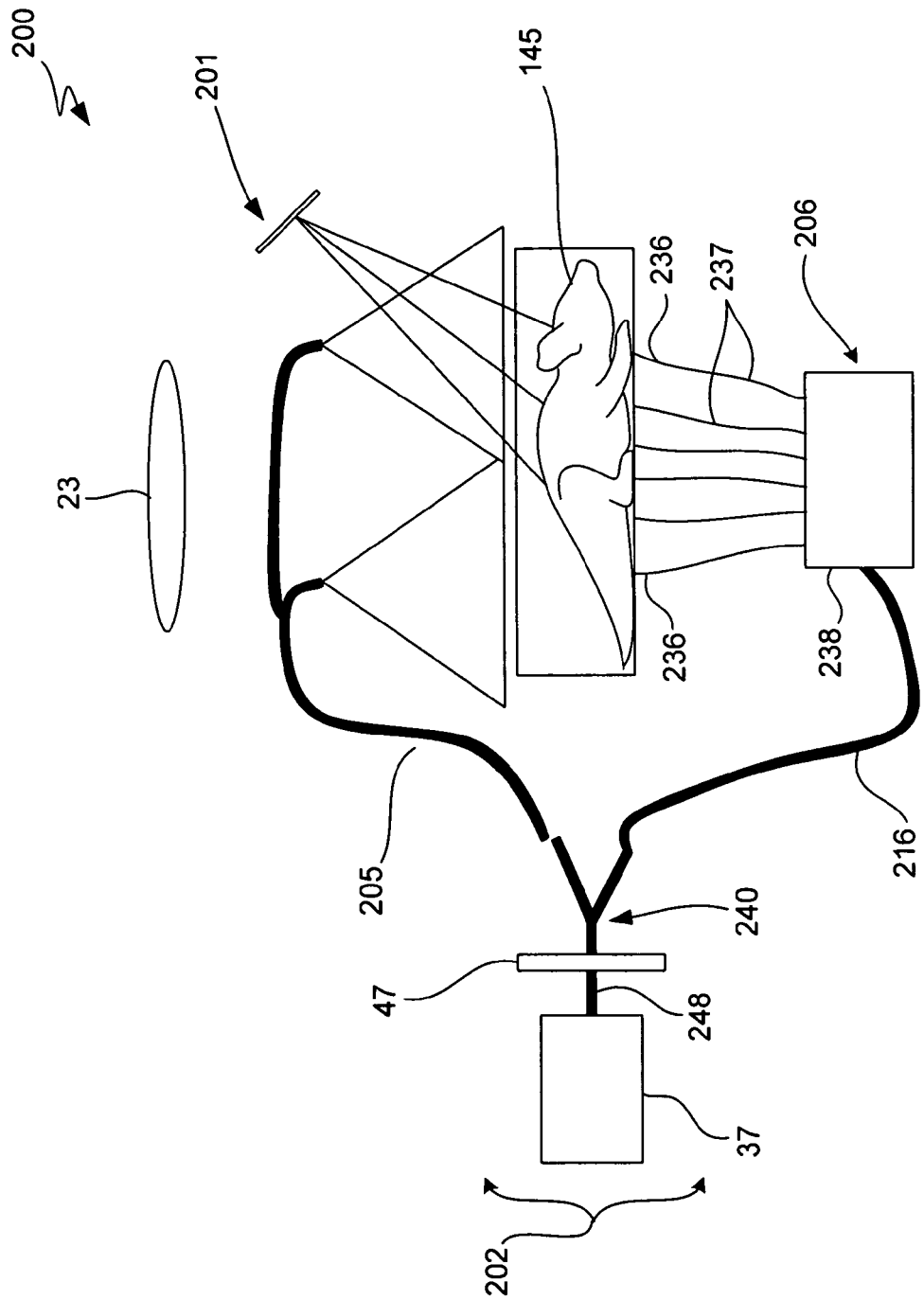
FIG. 12 is a schematic view of the dual illumination system of FIG. 10 with another alternative embodiment trans-illumination device.

Referring to FIGS. 10-12, a dual illumination system 200 is provided for use with the same imaging apparatus 21 (generally of FIGS. 1-9) disclosed in the embodiments described in detail below. Similar to those designs, the imaging apparatus at least defines a light-tight imaging compartment 25 with an interior wall 22 having a view port 23 extending therein. This view port 23 enables optical imaging data acquisition of a specimen contained in the imaging compartment. In this embodiment, the illumination system 200 includes a first illumination assembly, generally designated 201, that is configured measure the surface topography of a specimen, and a second illumination assembly, generally designated 202, that is configured to measure the either general or tomographical fluorescence. Briefly, the first illumination assembly is configured to direct structured light onto a first side of the specimen to enable structured light and surface topography measurements and/or data acquisition thereof. In contrast, the second illumination assembly 202 is configured to direct light at the specimen 145 wherein diffused fluorescent light emanates from a surface thereof, preferably facing the view port 23, for receipt therethrough to acquire fluorescence data of the specimen.

Accordingly, a single imaging apparatus is provided with a dual illumination system, the first illumination assembly of which applies structured light imaging to determine the 3D surface topography, and the second illumination assembly of which applies fluorescent excitation light to excite the fluorescent reporter. This is advantageous in that the 3D surface topography and fluorescence emission measurements can be performed on a single system. These measurements can then be applied in a fluorescence tomography algorithm to provide 3D localization information for the fluorescent source.

Briefly, In vivo fluorescence tomography refers to the technique of determining the location and brightness of a fluorescent reporter within a living research animal. Since photons in the visible to near-infrared part of the spectrum are strongly scattered in tissue, tomography techniques in this wavelength range utilize diffusion models for photon transport. Typically, a tissue specimen is illuminated with excitation light at several different locations and an image of the fluorescent light emission is acquired for each illumination location. These images are fed into a diffuse tomography code, which then localizes the source from the image information. By moving the illumination source relative to the embedded fluorescent reporter, additional accuracy on the localization of the source is achieved.

Typically, the best sensitivity is achieved by illuminating the specimen in a trans-illumination geometry. In the present inventive system, the source impinges on the specimen from the bottom (away from CCD camera), and light emission is imaged from the top side (toward CCD camera). The trans-illumination geometry gives improved sensitivity because auto-fluorescence generated by the tissue is reduced compared to an epi-illumination (reflection) geometry.

A requirement for executing a diffuse tomographic reconstruction algorithm is knowledge of the specimen surface shape, or surface topography. In order to measure surface topography, a structured light technique is utilized. Here a grid of lines is projected onto the animal at an angle of 20-30 degrees to the CCD camera optical axis. An image of the deflection of the lines passing over the specimen can be analyzed to determine the surface topography.

FIGS. 1-9 will now be described in detail to provide the requisite background imaging assembly foundation that the dual illumination system works in conjunction with. Hence, referring now to FIGS. 1-2 and 4, a fluorescence imaging assembly, generally designated 20, is provided which includes a light-tight sample box or imaging apparatus 21 having an enclosure wall or upper housing 22 defining a view port 23 (FIG. 4) into a light-tight imaging compartment 25 thereof. A specimen platform 26 is positioned in the imaging compartment 25 that includes a support surface 27 facing toward the view port 23. The imaging assembly 20 further includes an illumination assembly, generally designated 28, having an illumination device 30 disposed in the imaging compartment 25, and positioned proximate to and substantially peripherally encircling the view port 23 such that said specimen platform 26 is illuminated in a substantially uniform manner.

Figure 2:
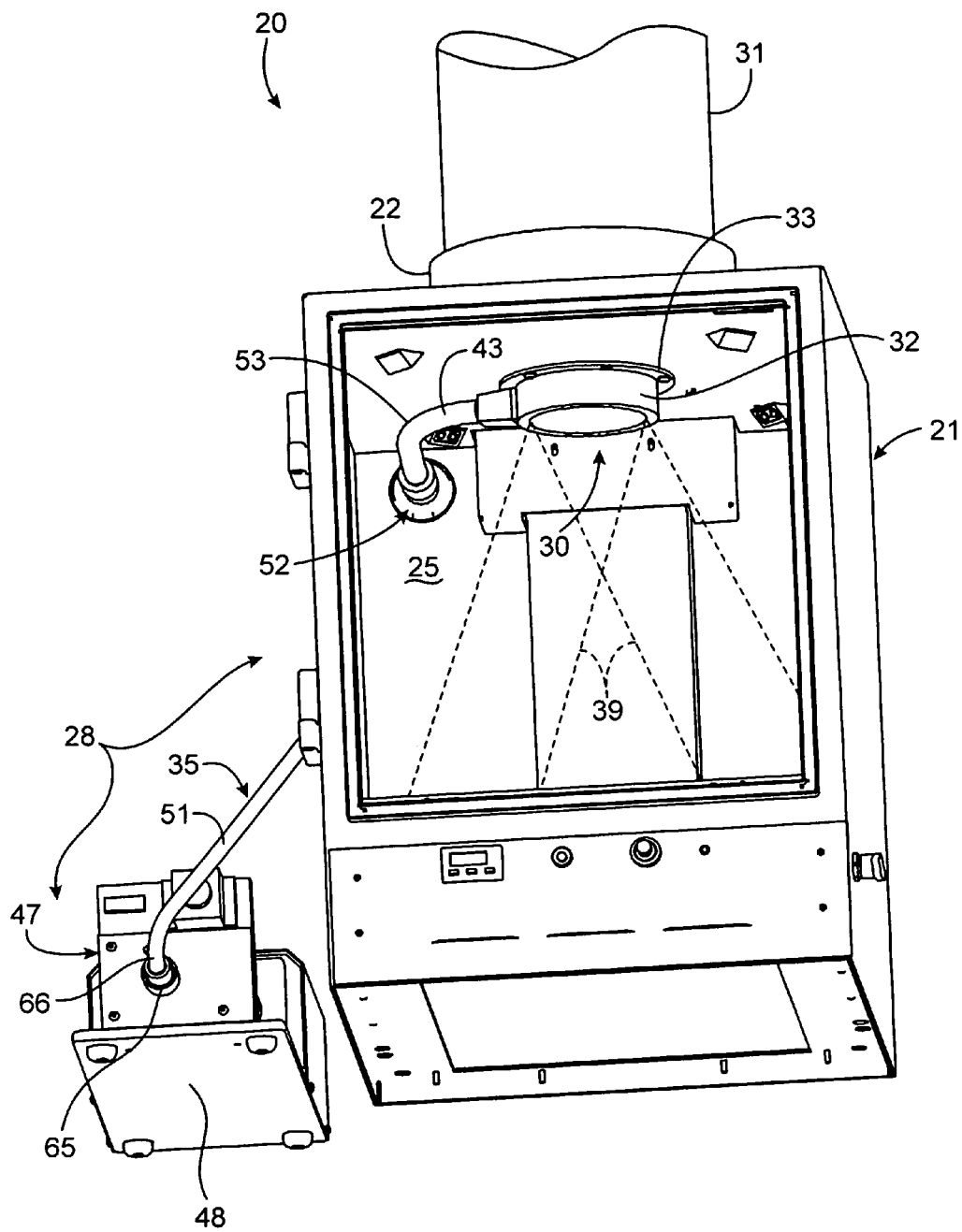
FIG. 2 is a bottom perspective view of the imaging apparatus of FIG. 1, and illustrating a light ring component of the illumination assembly.

Briefly, FIGS. 1 and 2 illustrate an imaging apparatus 21 suitable for capturing photographic, fluorescent or luminescence images in accordance with one embodiment of the present invention. The imaging apparatus 21 includes an upper housing 22 defining the view port in which a lens system of a high sensitivity camera 31 is mounted. This camera is preferably an intensified or cooled integrating Charge-Coupled Device (CCD) camera 31 which is positioned on top of the imaging apparatus 21 and positioned above the upper housing 22. The CCD camera 31 is capable of capturing fluorescent, luminescent and photographic (i.e., reflection based images) images of the sample within the imaging apparatus 21.

The illumination assembly 28 includes a frame 32 supporting the illumination device 30 that is mounted to the upper housing through a nut plate 33. The frame 32 is preferably a rigid, ring-shaped structure having an interior diameter slightly larger than that of the view port 23 so as to peripherally surround it without obstructing the view from the lens system. Although the illustrated illumination device and the supporting frame 32 are circular, other geometric forms may be applied as long as the illumination device extends generally around the view port 23.

In one specific embodiment, the illumination device is provided by a fiber optic lighting system having a plurality or bundle 35 of fiber optic strands extending into the imaging compartment 25. The proximal ends 36 of the strands of the bundle 35 are positioned in optical communication with a light source 37 to transmit collected light to the distal ends 38 of the fiber optic strands. To optimize the system for use fluorescent image capture in accordance with the present invention, the material composition of the fiber optic strands are selected to have low auto-fluorescence properties. One material particularly suitable for the fiber optic strands and filters is high purity fused silica, such as plastic clad fused silica or silica clad fused silica, which has very low autofluorescence. The distal ends of each independent strand, terminating at the illumination device, emit a conical directional beam of light which collectively form the substantially uniform conical beam (illustrated by broken lines 39) onto the specimen platform.

The direct light is provided by a bulb contained in the housing 45, and is positioned at the proximal end faces of the fiber optic strands. A preferred light comprises a tungsten halogen lamp, which emits a wide spectrum of bright white light suitable to fluoresce objects. Other applicable light sources include xenon lamps, mercury lamps and lasers.

Typically, the usable fluorescence spectrum is in the range of 400 nm to about 900 nm. Thus, depending upon the desired fluorescence spectra, the composition of the sample material and the fluorescent material, the remaining light emitted by the light source must be filtered out. Optical filters are applied, accordingly, to filter out non-fluorescence spectra as well as unwanted fluorescence spectra. Depending upon the application, there have been selected optical filters or filter wheels disposed in the imaging compartment of an imaging apparatus 21 just after the off-set light source. Such an arrangement, however, would not be practical in the lighting technique of the present invention since the diameter of the ring-shaped frame 32 is significantly larger. Moreover, proportionate to the size of the imaging compartment, a filter wheel could not be deployed.

Figure 4:
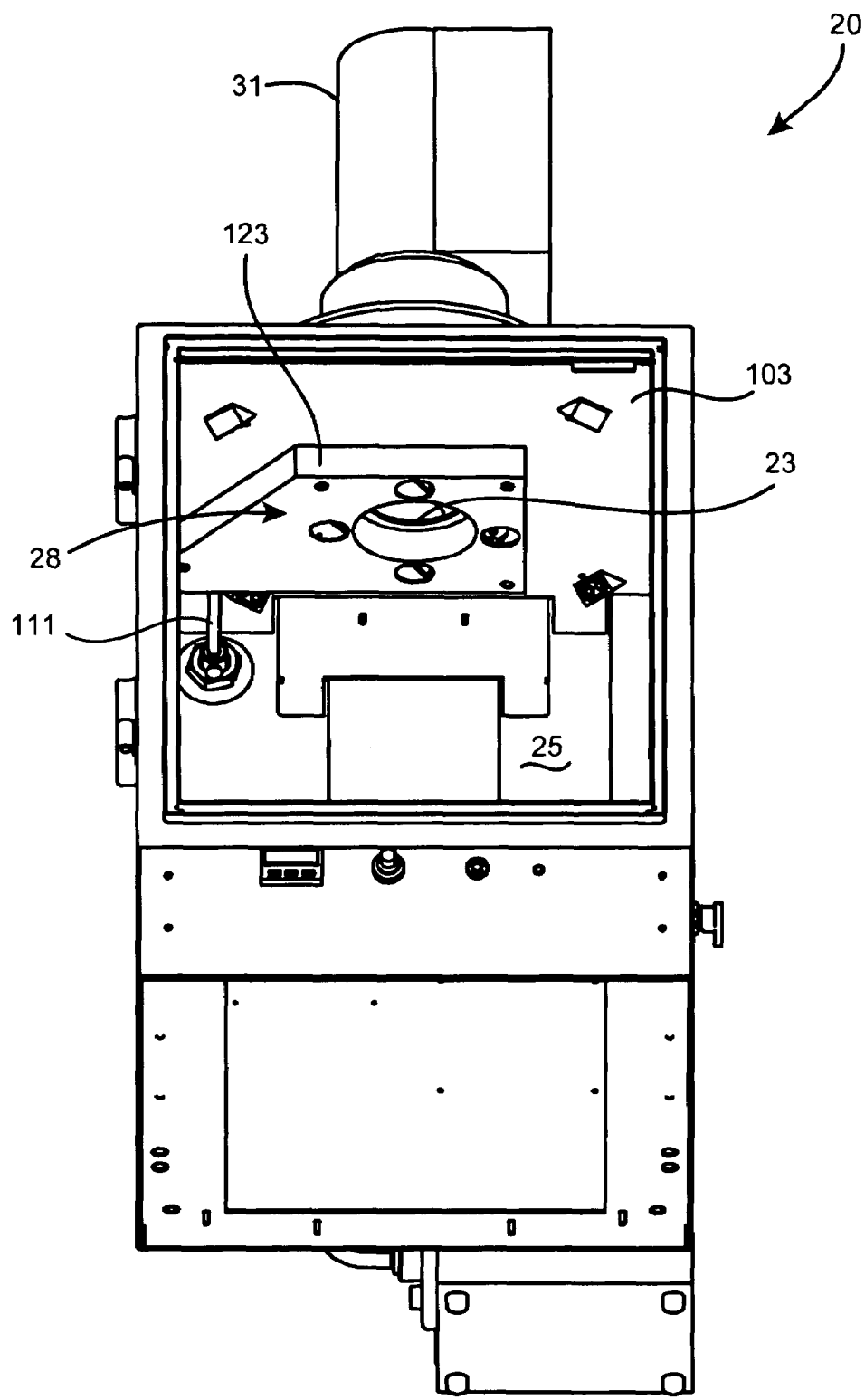
FIG. 4 is an enlarged, bottom perspective view of the imaging apparatus of FIG. 1, and illustrating an alternative embodiment illumination assembly.
Figure 6:
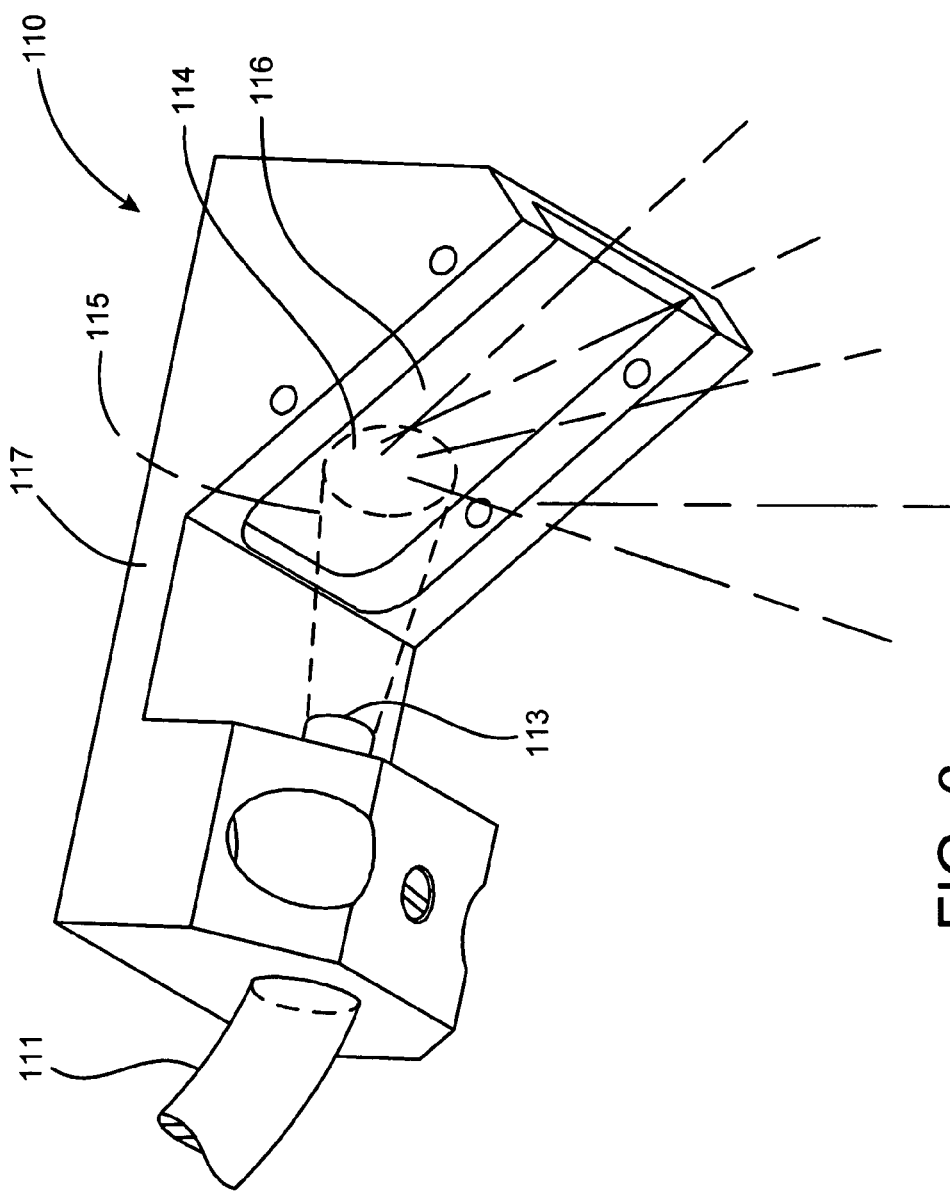
FIG. 6 is an enlarged, bottom perspective view of a light dispersion assembly of the illumination assembly of FIG. 4.

In accordance with the present invention, a filter wheel assembly, generally designated 47, is positioned "in-line" in the fiber optic bundle 35 (FIGS. 1, 4 and 6). Preferably, the filter wheel assembly 47, which includes a plurality of optical filters, is positioned in close proximity to the transmission box. This enables the filter wheel assembly and the transmission box to be supported on a common support frame 48, and to be packaged together as a single unit.

Figure 3:
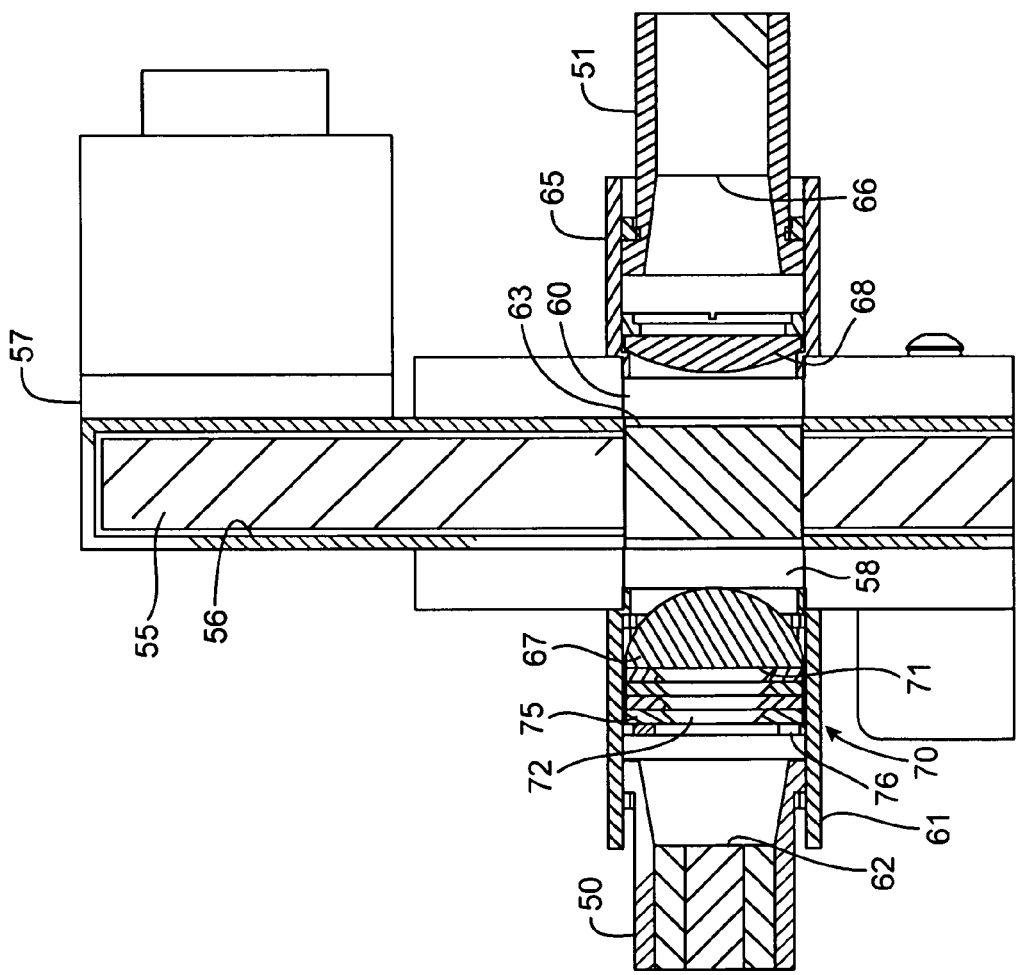
FIG. 3 is an enlarged, side elevation view, in cross-section, of the filter wheel assembly of the illumination assembly of FIG. 1.

Briefly, as best illustrated in FIGS. 2 and 3, the fiber optic bundle 35 includes a first bundle portion 50, extending between the light source 37 and the filter wheel assembly 47, and a second bundle portion 51, extending between the filter wheel assembly 47 and an optical connector assembly 52 mounted to the imaging apparatus 21. Finally, the fiber optic bundle includes a third bundle portion 53 extending from the optical connector assembly 52 (as will be described in greater detail below) on the inside of the imaging compartment 25 to the frame 32. This third bundle portion 53, as above-mentioned, includes the heat shrink material sleeve 43 that has low phosphorescence.

The optical filters are typically interference-type filters that include bandpass filters, longpass filters and shortpass filters. These filters are preferably provided as a filter set contained on a filter wheel 55 of the filter wheel assembly 47 that is placed in-line with the fiber optic bundle 35. Thus, the filter wheel 55, rotatably mounted in a recess 56 of the housing 57, can be selectively rotated to position the selected filter in the path of the fiber optic strands.

The housing, as viewed in FIG. 3, further includes an input port 58 and an output port 60 upon which the selected filter optically aligns therewith for the filtering of the light. Accordingly, a first connector 61 is included which is adapted to optically align an optical output end 62 of the first bundle portion 50 within the input port 58 of the housing for transmission of the light through the filter 63. Similarly, the filter wheel assembly 47 includes a second connector 65 that is adapted to optically align an optical input end 66 of the second bundle portion 51 within the output port 60 of the housing for reception of the filtered light from the filter 63.

To facilitate transmission of the light through the filter, a collimating lens 67 is positioned in the input port 58 between the optical output end 62 of the first bundle portion 50 and the filter 63. In order for the excitation filter to function properly, the light rays must be fairly well collimated (parallel to the optical axis) through the filter. Therefore, as the light passes through the collimating lens, it is collimated in a direction substantially perpendicular to the planar face of the filter that minimizes detrimental reflection there from. Further, by selecting the first bundle portion 50 of the fiber optic bundle 35, extending between the light source 37 and the filter wheel assembly 47, to be about ¼ inch in diameter, most of the exiting light rays have a maximum cone angle in the range of about 30° to about 40°. Consequently, after passing through the collimating lens 67, the angle of incidence is reduced to a maximum ray angle of less than or equal to about 12° The output of the excitation filter/illumination output device couples into the ½ inch diameter fiber optic bundle portion 51 in order to mate up with the ring light, which also as a ½ inch bundle size.

A focusing lens 68 is further disposed downstream from the filter 63 to focus and direct the collimated and filtered light, exiting the filter 63, into the optical input end 66 of second bundle portion 51 for transmission through the fiber optic strands thereof. FIG. 3 best illustrates that the focusing lens 68 is positioned in the output port 60 between the filter 63 and the optical input end 66 of the second bundle portion 51 of the fiber optic bundle 35. Typical of these filter wheel assemblies, by way of example, is model FA-448, by Acton Research of Acton, Mass. It will be appreciated, however, that light-tight filter cassettes and filter bars may be employed as well.

In accordance with another aspect of the present invention, a light baffle device, generally designated 70, is deployed between the optical output end 62 and the collimating lens 67 to intercept light these skewed light rays. Accordingly, the baffle device 70 will substantially prevent skewed rays from reflecting off of interior walls and entering the collimating lens 67 and thus leak around the filter 63.

The light baffle device 70, in one embodiment, includes an opaque plate member 75 disposed substantially adjacent an upstream abutting surface 71 of the collimating lens. Centrally disposed in the plate member is an aperture 72 extending there through, and having a transverse cross-sectional area smaller than that of the collimating lens abutting surface 71. Preferably, the ratio of the transverse cross-sectional area of the aperture 72 to that of the abutting surface 71 of the collimating lens 67 is in the range of about 0.64:1 to about 0.8:1.

FIG. 6 further illustrates that each plate member $75_A$-$75_D$ defines a respective central aperture $72_A$-$72_D$ which is co-axially aligned with the longitudinal axis of the abutting surface 71 of the collimating lens. A threaded ring 76 or the like is deployed in the input port 58 and matably engaged with the first connector 61 to affix the plate member $75_A$-$75_D$ against the abutting surface 71 of the collimating lens 67. Further, each aperture $72_A$-$72_D$ has a respective transverse cross-sectional area smaller than that of the collimating lens abutting surface 71. However, each adjacent downstream plate member $75_B$-$75_D$ defines a respective aperture $72_B$-$72_D$ having a diameter incrementally larger than its adjacent upstream plate member $75_A$-$75_C$. Preferably, the area of each successive downstream aperture $72_B$-$72_D$ is about 10% to about 25% larger.

Figure 5:
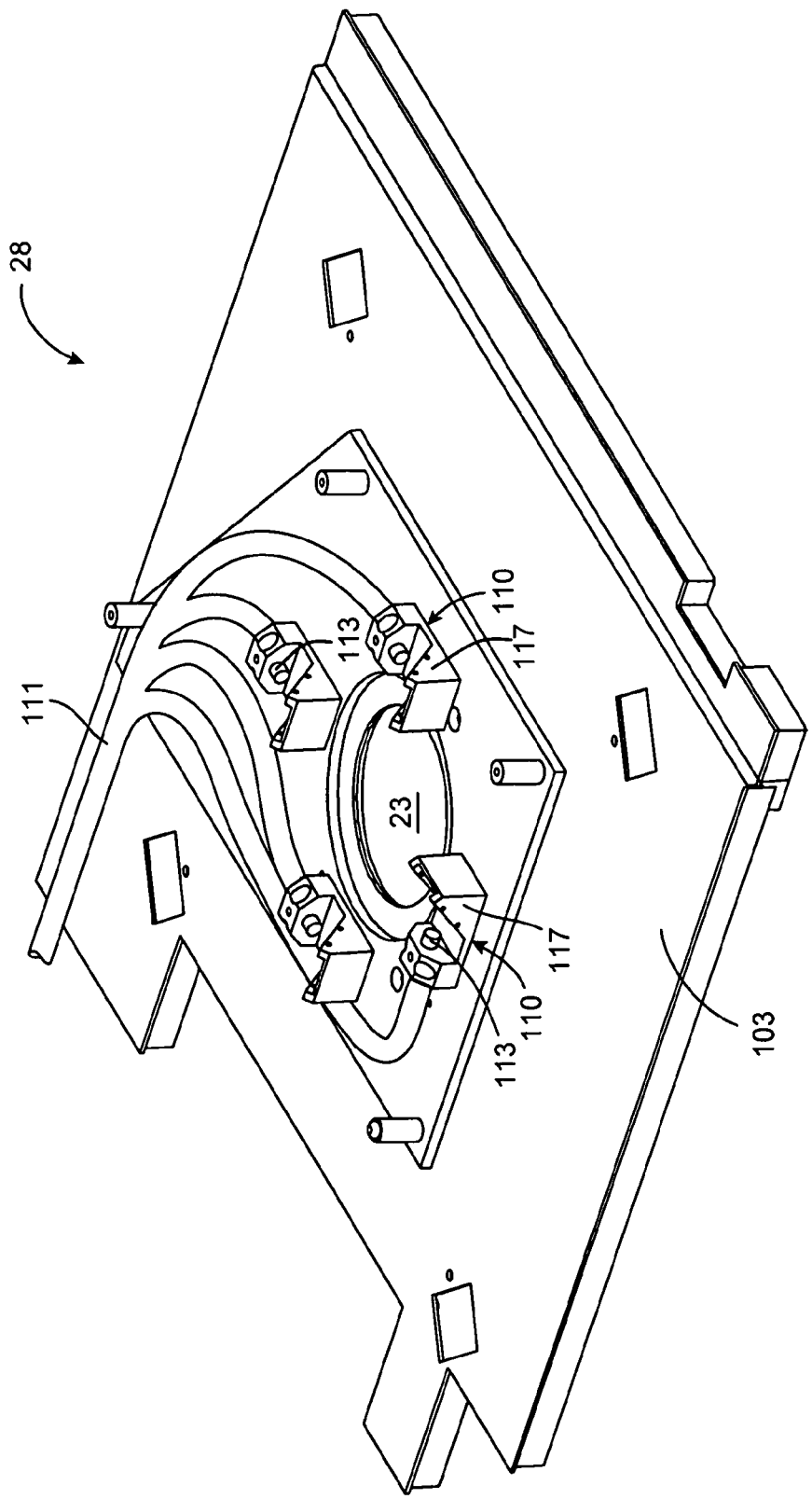
FIG. 5 is an enlarged, bottom perspective view of the alternative embodiment illumination assembly of FIG. 4 mounted to the upper interior wall of the imaging apparatus.
Figure 7:
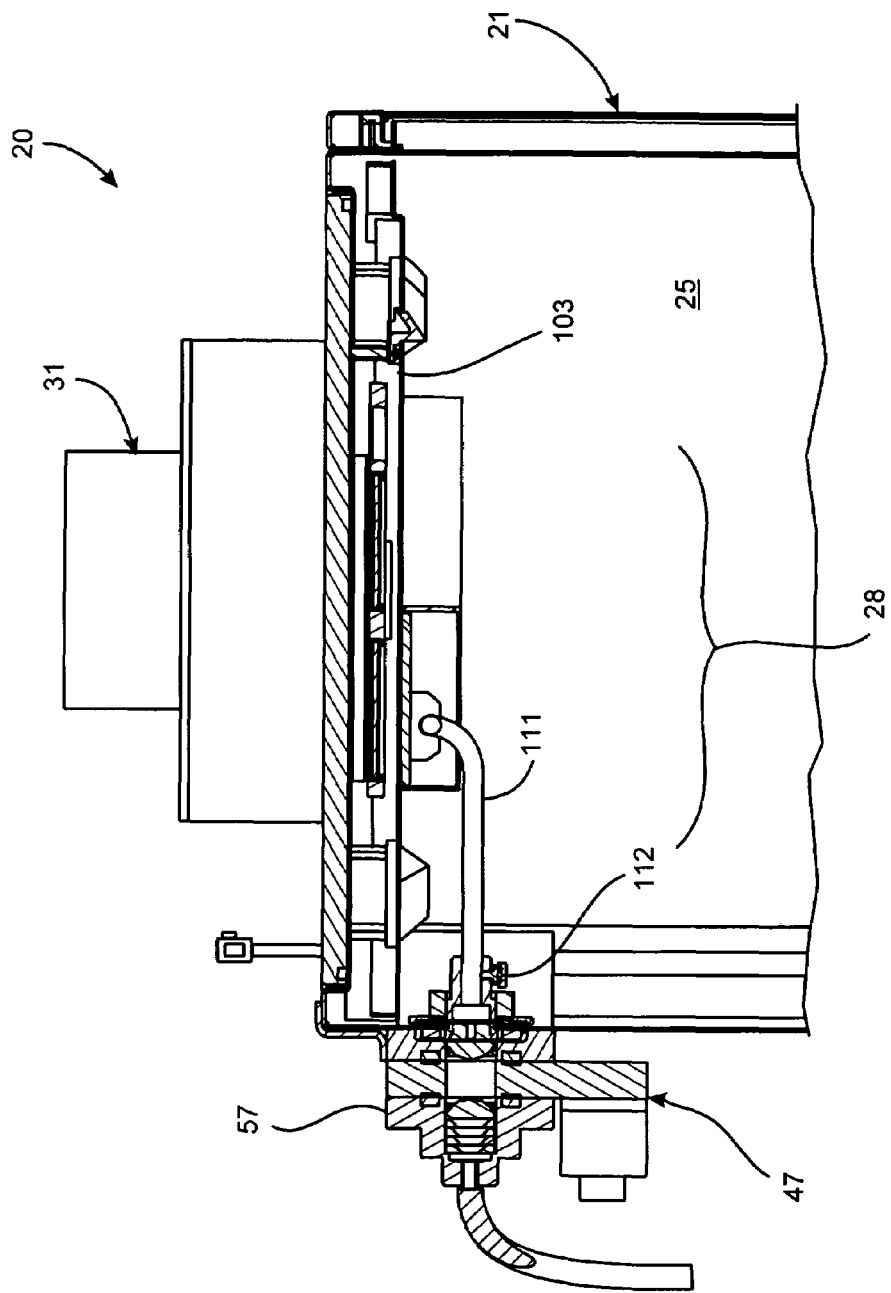
FIG. 7 is an enlarged, side elevation view, in cross-section, of the filter wheel assembly of the illumination assembly mounted to the imaging apparatus.

Referring now to FIGS. 4 5 and 7, another specific embodiment of the macroscopic fluorescence illumination assembly 28 is illustrated. In this configuration, the illumination assembly 28 includes a fluorescent light source 37, and a light dispersion assembly 110 positioned proximate the view port 23 of the interior wall 103. The illumination assembly 28 further includes a bundle 111 of fiber optic strands composed of substantially pure fused silica. The proximal ends 112 thereof in optical communication with the light source 37 and distal ends 113 thereof terminate proximate the view port 23. The distal ends 113 each emit a conical directional beam of light originating from the light source 37 and cooperating with the light dispersion assembly 110 such that the plurality of directional beams 115 (shown in phantom lines) collectively illuminate the specimen platform 26 in a substantially uniform manner.

The dispersion assembly 110 is configured to cooperate with the distal ends 113 of the fiber optic strands to redirect the directional beams 115 (shown in phantom lines) collectively toward the specimen platform 26 for illumination thereof in a substantially uniform manner. Accordingly, the optical axes of the distal ends 113 of the fiber optic strands may be retained generally parallel to the specimen platform 26, while the directional beams are directed (E.g., through reflective surfaces 116) downwardly toward the specimen platform 26. The overall height of the imaging apparatus 21, thus, is significantly reduced since the distal ends of the substantially pure fused silica fibers themselves need not be curved toward the platform 26, and the overall cost is significantly reduced.

Referring now to FIG. 6, the light dispersion assembly 110 includes a bracket device 117 adapted to mount and secure the distal ends 113 of the fiber optic strands to the upper interior wall 103 of the imaging apparatus 21. These bracket devices 117 are preferably substantially rigid, and are composed of black anodized aluminum to reduce auto fluorescence.

In one specific embodiment, to redirect the directional beams emitted from each distal end 113 of the strands, the dispersion assembly 110 includes a reflective surface 116 angled to reflect the directional beams toward the specimen platform 26. This permits the entire fiber optic bundle 111 to be maintained in generally the same plane that is essentially parallel to the specimen platform 26.

To reflect the directional beams about 90° from the optical axis of the distal ends of the strands and toward the specimen platform, the relatively planar reflective surface 116 should be oriented about 45° relative the direction of the optical axis. It will be appreciated that depending upon the particular position of the bracket device 117 and the exact orientation of the optical axis from the relative the desired position along the specimen platform to be illuminated, the angle of the reflective surface can be altered accordingly.

In one application, illumination "hot spots" can be reduced by diffusing the directional beams as they reflect off of the reflective surface 116. This improves the light distribution across the specimen platform so that the illumination is substantially uniform. One diffuser technique is to provide a diffusing surface 114 that cooperates with the reflective surface 116 to uniformly diffuse the directional beams emitted from the strand distal ends 113. For example, the reflective surface 116 may be provided by an aluminum plate with a roughened surface or by SPECTRALON®, which diffuses the reflected light as it impinges the surface thereof.

Figure 8:
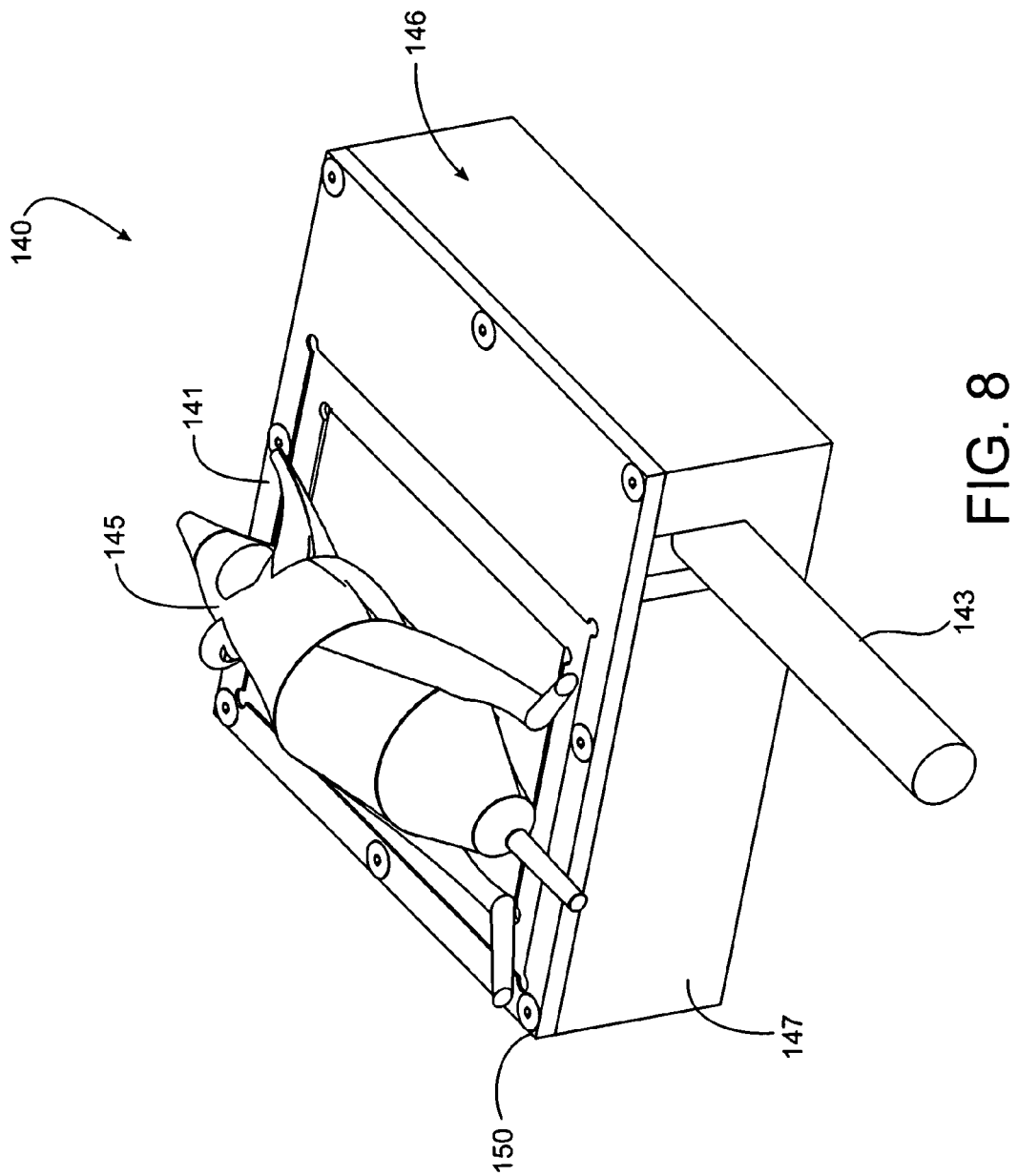
FIG. 8 is a top perspective view of an alternative embodiment bottom illumination assembly providing bottom illumination of the specimen constructed according to the present invention.

Referring now to FIGS. 8 and 9, in still another aspect of the present invention, an alternative embodiment macroscopic fluorescence illumination assembly, generally designated 140, is provided for use with the imaging apparatus 21. In this configuration, a bottom illumination configuration is provided that significantly reduces background fluorescent or autofluorescent signals emitted from the endogenous animal tissue itself.

The bottom side illumination assembly 140 is shown including a specimen support surface 141 sized and dimensioned for receipt in the imaging compartment 25 atop the specimen platform 26 of the imaging apparatus 21 (e.g., as shown in FIG. 1). The support surface 141 is substantially opaque and defines a window portion 142 that enables the passage of light there through which is oriented to face toward the view port 23 thereof. The window portion is selectively sized and dimensioned such that when the specimen is supported atop the support surface 141, it can be positioned and seated fully over the window portion in a manner forming a light-tight seal substantially there between. The illumination assembly 140 further includes an excitation light source 37, and a bundle of fiber optic strands 143 having proximal ends thereof in optical communication with the light source 37. The distal ends of the strands terminate proximate the window portion of the support surface. The distal ends each emit a respective beam of light originating from the light source 37 which are then collectively directed toward the window portion 142 and into a bottom side of the specimen 145.

In one specific configuration, the bottom illumination assembly 140 includes a specimen illumination platform, generally designated 146, having a support structure 147 and a cover plate 150 removably mounted atop the support structure. The support structure 147 is preferably rectangular shaped having four upstanding side walls 151 surrounding an interior cavity 152 thereof.

Mounted atop the upper edges of the upstanding walls 151 is the cover plate 150 that incorporates the support surface 141 to support the specimen 145. The cover plate 150 is also preferably composed of a rigid material such as black anodized aluminum to reduce autofluorescence.

Extending through the cover plate from the support surface 141 to a bottom side is an aperture 153 that enables the excitation light to pass from the interior cavity 152, and into the specimen. Thus, in some configurations, the aperture 153 functions as the window portion 142 of the support surface 141. This aperture is preferably rectangular shaped, but can be any size and/or shape to better coordinate with the shape of the specimen supported over the aperture. When the aperture 153 functions as the window portion, the specimen must be large enough to form a light-tight seal all around the edge of the aperture 153 when it is properly seated atop the support surface 141. Thus, essentially, the peripheral footprint of the aperture 153 must be sufficiently smaller than that of the properly oriented specimen 145 to form such a seal. It will be understood that without the formation of this light-tight seal between of the specimen with the edge defining the aperture, unscattered excitation light would leak into the imaging compartment 25 of the imaging apparatus 21 and be detected by the sensitive camera 31.

The distal ends 161 of the fiber optic bundle 143 terminate in the interior cavity 152 of the specimen illumination platform 146. A bundle slot 162 is provided in one of the upstanding walls 151 of the support structure 147 for receipt of the fiber optic bundle portion 143 there through. In one configuration, the distal ends 161 of the fiber strands of the fiber optic bundle 143 are oriented to direct the conical beams of light emitted there from directly through the window portion 142 and into the specimen seated thereatop.

Similar to the dispersion assembly 110 of the top illumination assembly above, a reflector device 163 is included in the interior cavity 152 of the support structure 147 that is configured to cooperate with the distal ends 161 of the fiber optic strands to redirect the directional beams collectively through the window portion 142 of the slide device 155. Accordingly, the optical axes of the distal ends 161 of the fiber optic strands may be retained generally parallel to the horizontal plane of the fiber optic bundle portion extending through the bundle slot 162 and into the interior cavity 152 of the support structure 147, while the directional beams emitted from the strand distal ends are reflected (E.g., through reflector device 163) upwardly through the window portion 142 and into the specimen 145. The overall height of the bottom illumination assembly 140 can, thus, be significantly reduced since the distal ends of the fibers themselves need not be curved upward toward the window portion.

Referring now to FIGS. 10-12, the dual illumination system 200, upon which this application is primarily based, is provided for use with the same imaging apparatus 21 disclosed in the above-mentioned embodiments. Similar to those designs, the imaging apparatus at least defines a light-tight imaging compartment 25 with an interior wall 22 having a view port 23 extending therein. This view port 23 enables optical imaging data acquisition of a specimen contained in the imaging compartment. In this embodiment, the illumination system 200 includes a first illumination assembly, generally designated 201, that is configured measure the surface topography of a specimen, and a second illumination assembly, generally designated 202, that is configured to measure the either general or tomographical fluorescence. Briefly, the first illumination assembly is configured to direct structured light onto a first side of the specimen to enable structured light and surface topography measurements and/or data acquisition thereof. In contrast, the second illumination assembly 202 is configured to direct light at the specimen 145 wherein diffused fluorescent light emanates from a surface thereof, preferably facing the view port 23, for receipt therethrough to acquire fluorescence data of the specimen.

Accordingly, a dual illumination system is provided for an imaging apparatus. In the first illumination assembly, structured light is applied for surface topographic imaging of a specimen. By analyzing an image of structured light projected onto the specimen, the surface topography of the specimen positioned atop the specimen platform 26 in the imaging apparatus 21 can be constructed. The second illumination assembly 202 is then applied to fluoresce the specimen, as will be described. However, using the surface topographic data of the specimen determined by the first illumination assembly 201, in one embodiment, the surface topography of the specimen can be determined, relative to the support surface. Collectively, these two illumination assemblies cooperate with one another to provide the information necessary to perform a 3D diffuse fluorescence tomography and thereby localize the source of fluorescence within the specimen.

The first illumination assembly 201, in accordance with the present invention, applies a light source for 3-D imaging of a specimen. In particular, a scanning laser galvanometer is applied for structured light and surface topography determinations of the specimen, although the structured light source may be provided by a light projector (not shown) as well. For example, a projection device may be employed consisting of Ronchi ruling that is illuminated by an LED and optically projected onto the specimen.

Figure 23:
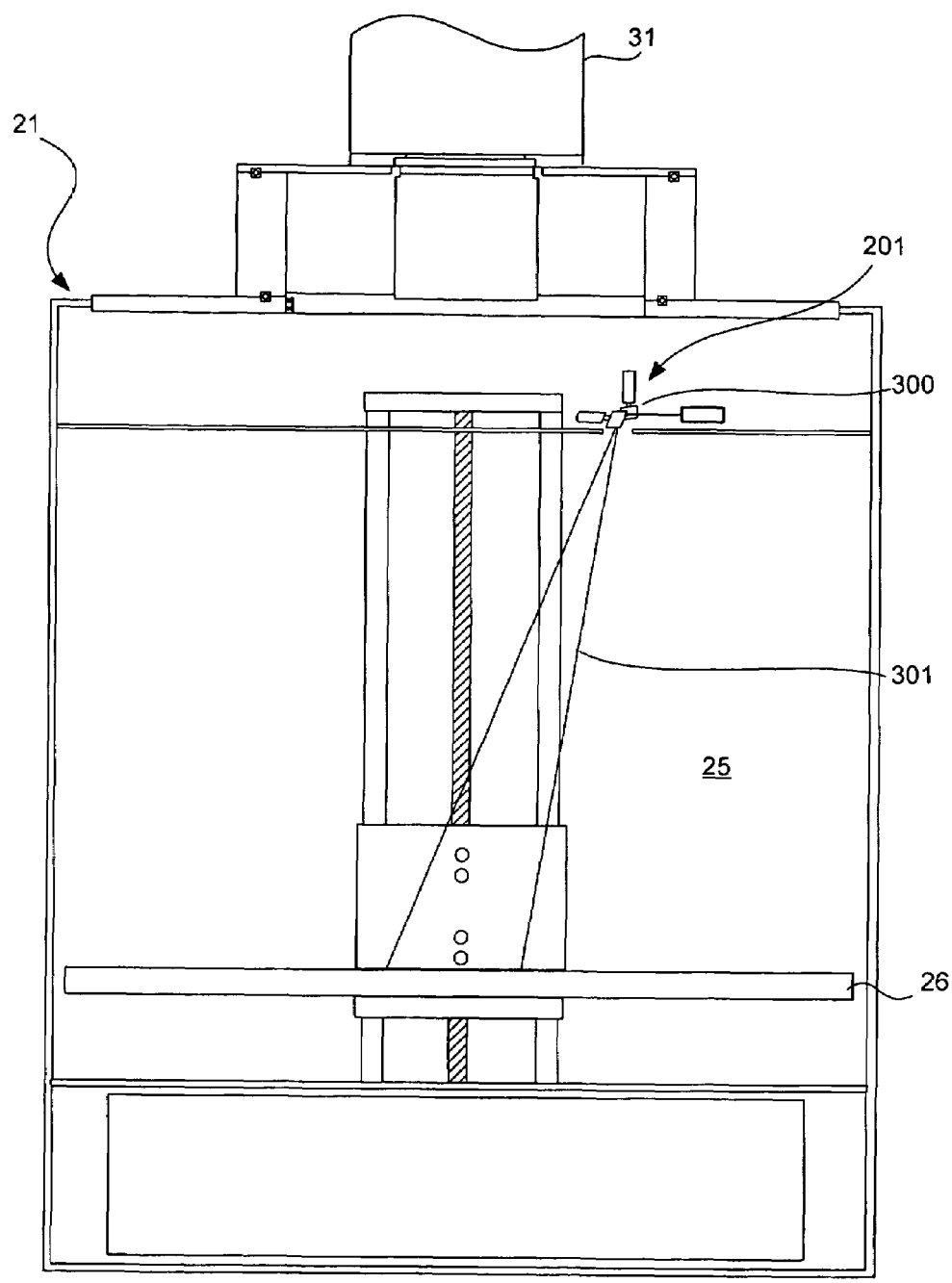
FIG. 23 is an enlarged, side elevation view, of an imaging apparatus of the present invention incorporating a scanning laser galvanometer as the first illumination system.
Figure 24:
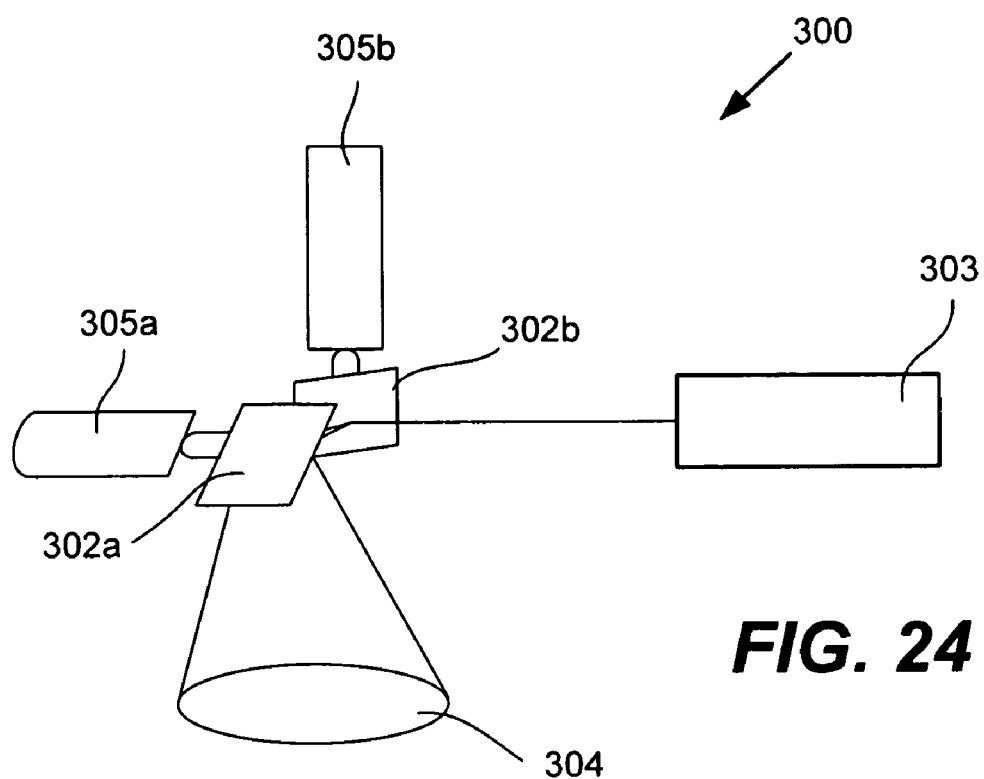
FIG. 24 is an enlarged, side elevation view, of a structured light source for the scanning laser galvanometer of FIG. 23.

Referring to FIG. 23, however, scanning laser galvanometer 300 is disposed at the top of imaging chamber 25 and reflects structured light 301 down onto a top surface of the animal. Referring to FIG. 24, scanning laser galvanometer 300 comprises a laser 302 and a pair of mirrors 303a and 303b, and projects structured light onto the top surface of stage 26. The grid size produced on stage or platform 26 (or an animal resting thereon) will depend on position of stage 26 and control of each mirror 303 according to a desired grid size.

Laser 302 generates light. Mirrors 303 each direct light provided by laser 302. The two mirrors 303 cooperate to provide two degree of freedom control for positioning a light beam provided by laser 302. A maximum transmission field 304 defines the spatial range for direction of light by scanning laser galvanometer 90. Actuators 305a and 305b position mirrors 303a and 303b respectively, and may create any line, shape, grid or pattern of light within field 304. For example, actuators 305 and mirrors 303 may form a set of parallel lines normal to the head to toe facing of a mouse (for any position of the mouse).

In general, the light output by a structured light source may include any lines or shapes suitable for generating structured light surface information that is useful in building a surface topography. In one embodiment, a structured light source transmits a grid of lines onto the animal. Spacing between lines in a parallel grid may be adapted to a specific object or image. A parallel grid of lines having line spacing in the range of about 0.2 to about 2 lines per mm is suitable for a mouse. Other line spacings are suitable for use with the present invention. The line spacing may vary based on the object surface texture and object size. Closer line spacing provides higher resolution. As mentioned above photographic information may be used offset limitations of structured light at high resolutions, thus enabling even closer spaced structured light lines and more accurate surface representations.

Such a structured light system is detailed in our U.S. patent application Ser. No. 11/127,346, filed May 11, 2005, by Rice et. al. and entitled "3-D IN-VIVO IMAGING AND TOPOGRAPHY USING STRUCTURED LIGHT", which is a continuation application of U.S. application Ser. No. 10/606,976, filed Jun. 25, 2003, by Daniel G. Stearns et al. and entitled, "METHOD AND APPARATUS FOR 3-D IMAGING OF INTERNAL LIGHT SOURCES", both of which are incorporated by reference in their entirety. These applications also claim priority under 35 U.S.C. §119(e) from U.S. Provisional Applications No. 60/395,357, entitled "Method and Apparatus for 3-D Imaging of Internal Light Sources", by Daniel G. Steams, et al.; U.S. Provisional Application No. 60/396,458, entitled "In Vivo 3D Imaging of Light Emitting Reporters", by Bradley W. Rice, et al.; and U.S. Provisional Application No. 60/396,313, entitled "3D in Vivo Imaging of Light Emitting Reporters", by Bradley W. Rice, et al. These provisional applications were all filed on Jul. 16, 2002 and are also incorporated by reference for all purposes.

The second illumination assembly 202, as mentioned, is applied for fluorescence imaging of the specimen. In accordance with the present invention, either epi-illumination or trans-illumination techniques, or both, can be applied to fluoresce the targeted tissue of the specimen. In one specific embodiment, epi-illumination, which is preferably reflection-mode imaging, is provided by an epi-illumination device 203 (i.e., emitting white light or UV such as the above disclosed epi-illumination designs) is applied which involves reflecting an excitation light off the targeted surface of the specimen to generate contrast (absorption) for white light applications, e.g., colorimetric membranes (opaque); or excitation by filtered light (via filter wheel assembly 47) to measure fluorescence emission. By way of example, the above-mentioned epi-illumination device 203 may be applied by the light-ring embodiment 30 shown in FIG. 2, or by the plurality of light dispersion assemblies 110, shown in FIGS. 4-7, disposed about the view port 23. Briefly, a remote excitation light source is optically coupled to the epi-illumination device 203 (or devices) through a first light transmission unit 205. As has been described, and as will again be described below, the first light transmission unit 205 is preferably provided by a plurality or bundle of fiber optic strands extending into the imaging compartment 25. Proximal ends of the strands are in optical communication with a remote excitation light source, while a distal end of the strands terminates at the epi-illumination device 203.

In accordance with the present invention, generally fluorescence imaging, or tomographic fluorescence imaging, of the second illumination assembly 202 may also be acquired by a trans-illumination technique, which involves transmitting an excitation light (i.e., UV through infrared light) through the specimen. Similar to the epi-illumination device, a trans-illumination device 206 emits excitation fluorescence energy in the UV range to near infrared range (about 400-900 nm) that causes fluorescence emission.

In one specific embodiment, the trans-illumination device may be applied using the bottom trans-illumination assembly 140 shown in FIGS. -8 and 9. In this configuration, however, an entire surface section of the specimen that is placed over the window portion 142 is trans-illuminated simultaneously. While this is advantageous to observe large sections of the specimen simultaneously, it does not provide 3D localization (tomographic) data.

Accordingly, in another specific embodiment of the present invention, the trans-illumination device 206 is provided by one or more point sources of light beams that are applied to pinpoint illuminate the specimen at strategic locations thereof. The fluoresced excitation light exits the specimen surface facing the view port 23, and is detected by the imaging sensor of the camera.

This pinpoint illumination technique is advantageous in that moving the illumination point relative to a fixed fluorescent source provides 3D tomographic localization information. However, since this trans-illumination design is only capable of pinpoint illumination, multiple point illuminations about the surface of the specimen are necessary to properly scan the entire specimen. Hence, either the specimen and/or specimen platform 26 can be reoriented relative to a beam output end 210 of the trans-illumination device 206 or the beam output end is capable of reorientation relative to the specimen and/or specimen platform 26.

Figure 13:
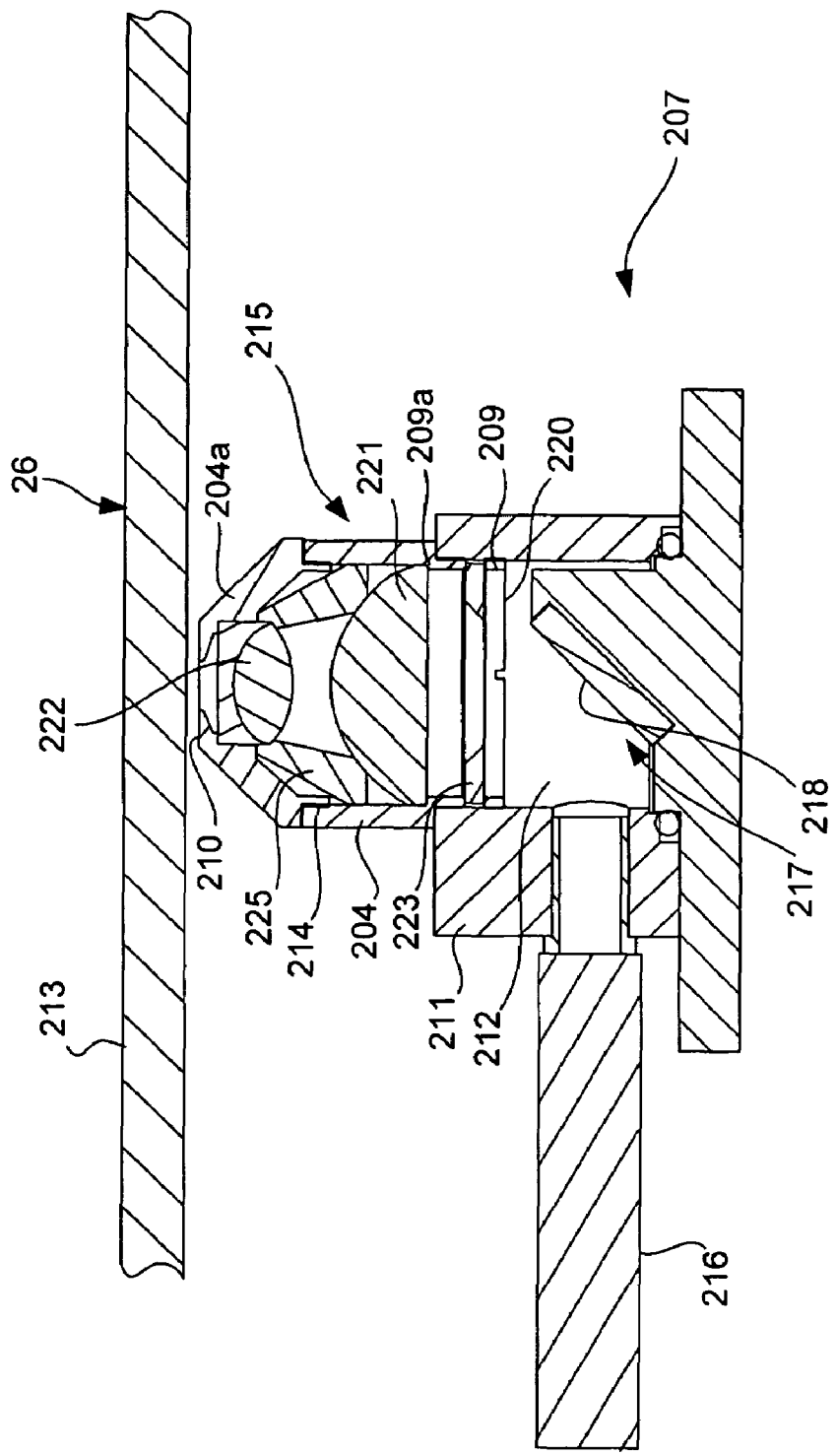
FIG. 13 is an enlarged, side elevation view, in cross-section, of a low profile illumination output device of the illumination system of FIG. 10.

Referring now to FIGS. 10 and 13, in the preferred form, a trans-illumination device 206 is provided having a low profile illumination output device 207 coupled to a movable translation platform 208. This platform is capable of positioning the output end 210 of the illumination output device 207 at one of a plurality of positions adjacent a surface of the specimen. Briefly, the low profile footprint of the trans-illumination device 206 enables positioning thereof under the specimen platform 26 in a relatively tight access space. In turn, the overall height footprint of the imaging apparatus 21 can also be reduced or minimized.

The illumination output device 207 includes a housing 211 that defines an interior cavity 212 therein. To reduce the overall height footprint, the excitation light entering the illumination output device is redirected from one direction to another direction toward a window portion 213 of the specimen platform 26. After redirection of the excitation light, the output device 207 includes a lens assembly 215 to focus the redirected excitation light into a smaller beam of light onto a surface of the specimen 145.

As best viewed in FIGS. 10 and 13, the excitation light is transmitted to the cavity of the housing 211 through a second light transmission unit 216 and a remote excitation light source 37. Similar to the above-mentioned trans-illumination and epi-illumination devices, the light second transmission unit 216 is provided by a plurality or bundle of fiber optic strands having proximal ends positioned in optical communication with a remote light source 37, and distal ends terminating in the interior cavity 212 of the output device housing 211. The composition of the fiber optic strands is selected to minimize or to have low auto-fluorescence properties, such as those containing high purity fused silica (e.g., plastic clad fused silica or silica clad fused silica).

In accordance with the present invention, it is desirable to minimize overall height footprint of the illumination output device 207. Entering the cavity 212 of the housing 211 at a direction toward, and substantially perpendicular, to the window portion 213 would maximize the height footprint rather than minimize it. Moreover, due to the relative stiffness of the fiber optic bundle, the bending radius thereof is relatively large. Accordingly, the overall height footprint has been significantly reduced by optically redirecting the excitation light output from the distal ends of the second transmission unit 216 toward (vertically in this example) and in the direction of the window portion. Essentially, in this specific embodiment, the direction of the excitation light is optically redirected about 90° from a substantially horizontal direction, entering the housing 211, to a substantially vertical direction toward the window portion 213 of the specimen platform 26.

FIG. 13 shows that the distal end of the light transmission unit 216 enters the housing 211 and terminates in the cavity 212 generally in a substantially horizontal orientation. Accordingly, the emission of the excitation light from the distal end of the fiber optic strands are also generally in the horizontal direction. To optically redirect the excitation light, an optical element 217 is positioned in the cavity 212, just downstream from the distal ends of the fiber optic strands, and in alignment with the exiting excitation light. Preferably, the redirection of the excitation light is about 90° from the generally substantially horizontal direction towards the substantially vertically direction so as to be substantially perpendicular to the window portion 213 of the specimen platform 26.

This reflective application structurally facilitates maintaining a low profile footprint of the illumination output device. To reflect the directional beams about 90° from the optical axis of the distal ends of the strands and generally perpendicular to the specimen platform 26, the relatively planar reflective surface 218 should be oriented at about 45° relative to the direction of the optical axis. This enables the entire fiber optic bundle (i.e., the second transmission unit 216) to enter the housing 211 at a substantially horizontal orientation that is essentially parallel to the specimen platform 26. It will be appreciated that depending upon the exact orientation of the optical axis relative to the desired orientation of the output beam along the specimen platform to be illuminated, the angle of the reflective surface can be altered accordingly.

In accordance with the present invention, the illumination output device 207 is configured to focus the redirected excitation light into a pinpoint beam, through the window portion 213 of the specimen platform, and onto a surface of the specimen. Accordingly, by positioning the pinpoint beam emitted from the output end 210 at a plurality of strategic locations about the surface of the specimen supported by the window portion, strategic trans-illumination can be performed as the diffused light fluoresces the targeted tissue and exits the opposite surface of the specimen.

To focus the excitation light manipulated by the optical element 217, as mentioned, a lens assembly 215 is disposed in the output device housing 211 in the path of the manipulated light. The lens assembly 215 includes a cylindrical base 204 with a cap member 204a at the output end, and opposite an input end 220 configured to mount to the housing 211. The lens assembly 215, briefly, collects the manipulated light reflecting from the reflective surface 218, in one embodiment, and then output the focused light from the output end 210 thereof.

FIG. 13 best illustrates that the lens assembly 215 is comprised of a two lens system containing a proximal plano-convex lens 221 and a bi-convex achromatic lens 222 spaced-apart from the plano-convex lens 221. Briefly, the plano-convex lens 221 functions to collect the light reflected from surface 218, while the spaced bi-convex achromatic lens 222 functions further focus the light from the plano-convex lens 221 into a pinpoint beam at a selected focal point. Alternatively, the bi-convex achromatic lens can be replaced by a spherical lens to produce a pinpoint beam of a different size. Collectively, these two lenses cooperate to focus the excitation light into a pinpoint beam a predetermined distance from the output end 210 of the illumination output device 207. Accounting for the distance of the output end 210 from the bottom of the window portion 213 of the specimen platform 26, the thickness of the window portion, and the average position of the surface of a specimen from the top surface of the window portion, the position of the focal point of the pinpoint beam can be calculated. For example, this distance can range from about 0.1 mm to about 3.0 mm.

Disposed within the base 204 of the lens assembly 215, at the input end 220, is a proximal baffle device 223 similar to the light baffle device 70 disclosed above in reference to the filter wheel assembly 47. This proximal baffle is supported between a lower annular support member 209 and a lower annular edge portion of the cylindrical base 204. Similarly, the plano-convex lens 221 is supported atop an annular shoulder portion 209a of the base 204 and a lower portion of the intermediary baffle device 225.

Further, in between the plano-convex lens 221 and the bi-convex achromatic lens 222 is an intermediary baffle device 225. This intermediary baffle 225 is supported atop a lower annular support device member 214 and the cap member 204a. Collectively, the cap member 204a and the upper portion of the intermediary baffle device 225 sandwiches the bi-convex achromatic lens 222 therebetween for support thereof.

As indicated above, these baffles devices 223, 225 intercept skewed light rays, and substantially prevent them from reflecting off of the housing interior walls defining the cavity 212. Hence, these skewed light rays are further prevented from leaking around either lens.

Applying the same concepts, designs and physical properties described in the light baffle device 70, and further incorporated herein, both the proximal baffle device 223 and intermediary baffle device 225 can be provided by one or more plate members. These are disposed substantially adjacent one another, and include centrally disposed apertures having a transverse cross-sectional area smaller than that of the respective plano-convex or bi-convex achromatic lens at their widest cross-sectional dimensions. In both the proximal and intermediary baffle designs 223, 225, the diameter of the respective aperture of each adjacent plate member is smaller than its adjacent, distal plate member. Collectively, as shown, the apertures taper inwardly toward respective lens 221, 222.

Due in-apart to the application of a pinpoint beam of excitation light, as compared to the diffused light, applied in the embodiments of FIGS. 8 and 9, it is not necessary to size and dimension the window portion 213, so as to form a light-tight seal with a surface of the specimen supported thereatop, but may be sized close to the footprint of the subject specimen to minimize light leakage around the specimen. In other words, the size of the window portion 213 may exceed the size of the footprint of the targeted specimen (FIG. 10). Not only does this easy placement of the specimen atop the window portion 213, but also facilitates the application of a more universally sized window portion 213. Hence, the window portion 213 can essentially extend nearly across the entire support surface of specimen platform and/or be integrally formed therewith. Of course, faceplates with apertures may be applied, as shown above, if necessary. Further, to reduce reflection, the window portion may include an anti-reflective coating as well.

While the pinpoint beam of excitation light exiting the output end 210 for the illumination output device 207 is significantly more intense, it does not apply to a large region of the specimen, as compared to a more diffuse light application in the trans-illumination embodiments of FIGS. 8 and 9. Rather, the trans-illumination observed is more local, depending upon the region of entrance relative to the specimen. Accordingly, as mentioned, a plurality of measurements can be performed at strategic locations along the targeted surface of the specimen.

Figure 14:
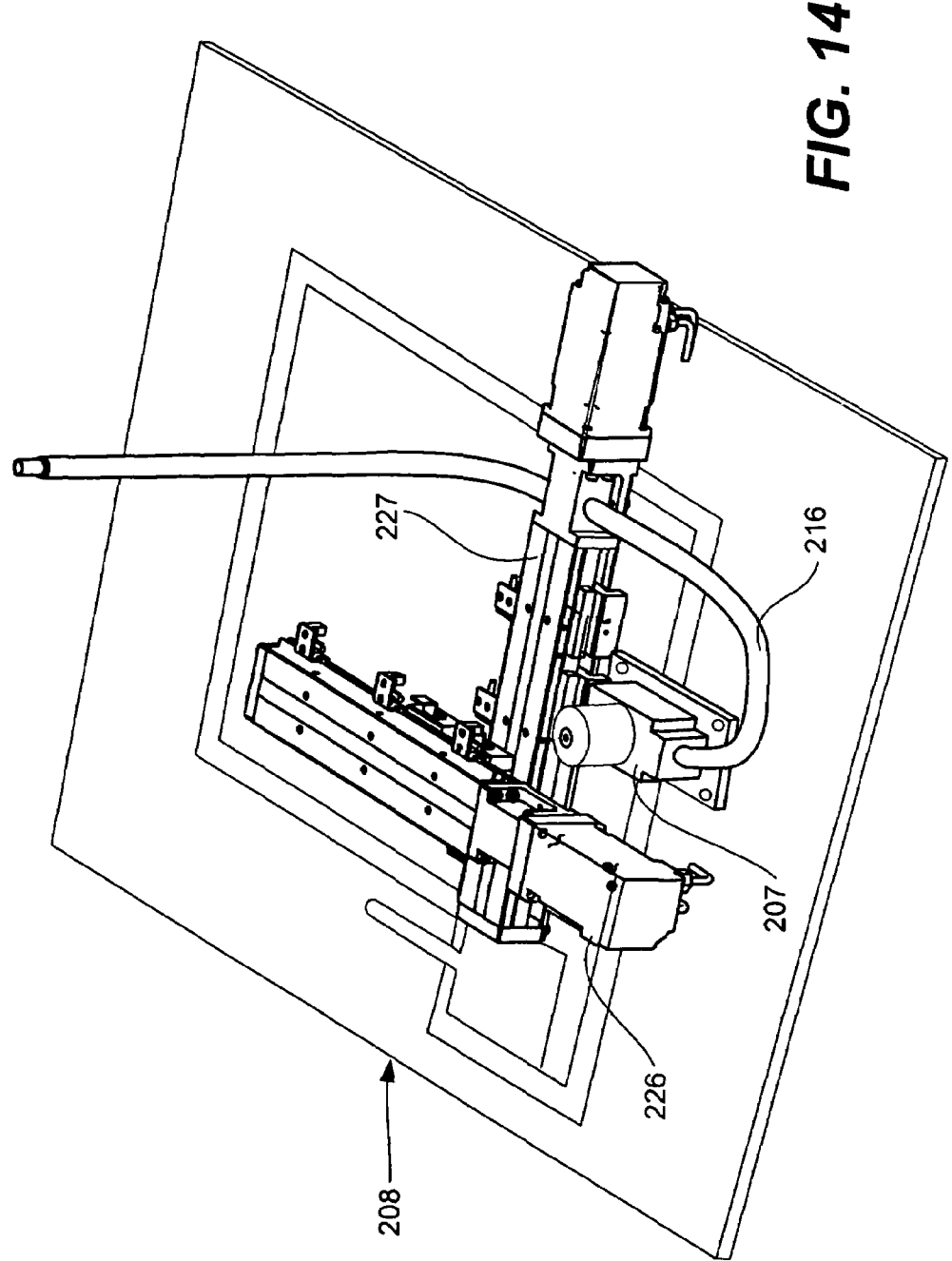
FIG. 14 is a reduced top perspective view of a translation platform movably supporting the low profile illumination output device of the illumination system of FIG. 10.
Figure 15:
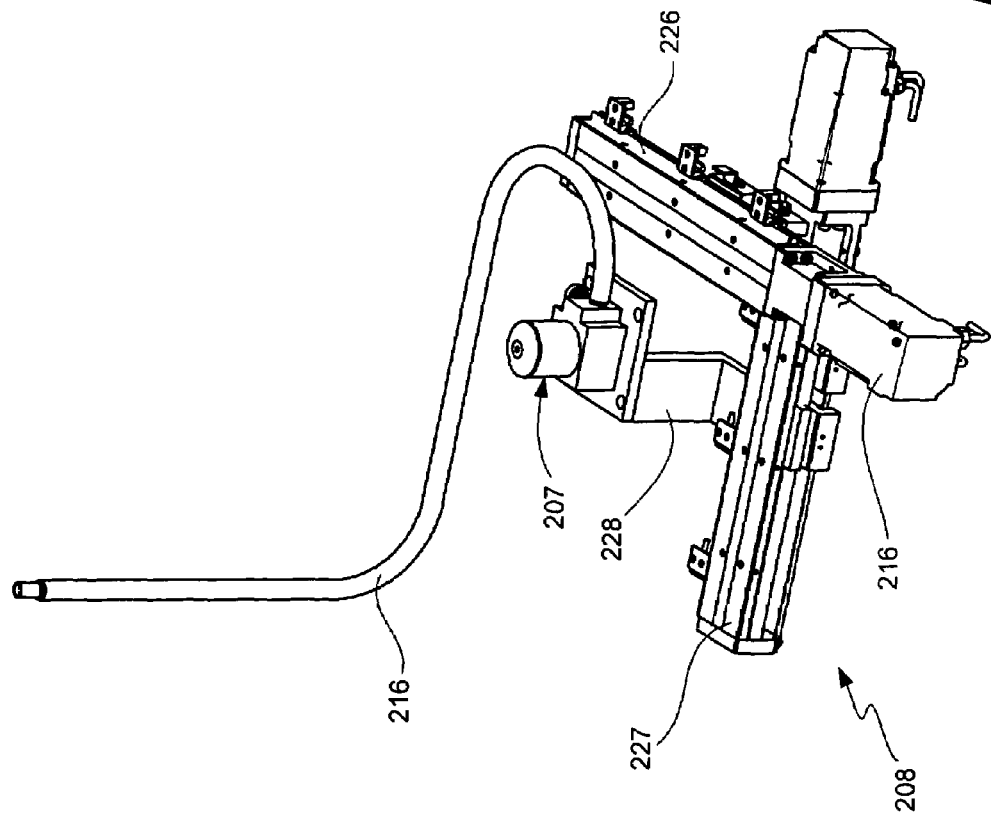
FIG. 15 is a top perspective view of X-arm and Y-arm of the translation platform of FIG. 14, and illustrating a mounting bracket for mounting the output device to the Y-arm.

In accordance with this embodiment of the present invention, however, in order to strategically position the pinpoint beam of excitation light at the predetermined location, the illumination output device 207 cooperates with a translation platform 208 positioned under the specimen platform 26. While a variety of translation mechanisms can be employed, a more conventional X-Y Translation platform is shown and illustrated. As best viewed in FIGS. 10, 14 and 15 the translation platform 208 includes an elongated horizontal or X-arm 226, and an elongated vertical or Y-arm 227, both of which are rail mounted to a translation platform 208. Applying a mounting bracket 228, the low profile illumination output device 207 is secured to one of the translation arms (e.g., Y-arm 227 in FIG. 15). Accordingly, through conventional control means, the translation arms 226, 227 and the mounting bracket 228 cooperate to selectively position the output end of the illumination output device at one of a plurality of positions adjacent the window portion 213 such that the light beam impinges the targeted surface of the specimen at one of a plurality of positions therealong.

One example of such a translation platform 208 is that provided by Model No. BG2005A, by Nippon Bearing Co. of Japan.

Figure 16:
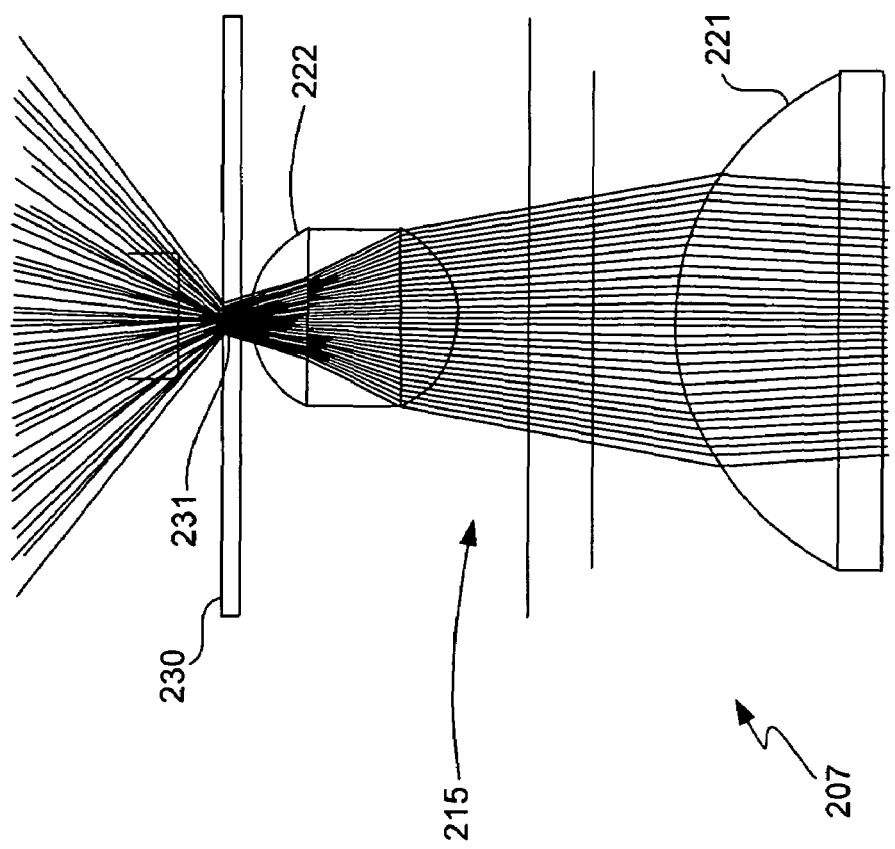
FIG. 16 is an enlarged side elevation view of the low profile illumination output device of FIG. 13 in an alternative application with a well plate cell.

In an alternative application of the trans-illumination device 206, an opaque specimen tray 230 may be positioned atop the window portion 213 of the specimen platform 26, containing an array of well plates 231 therein (FIG. 16). For example, a standard 96 well plate tray 230 may be applied where each well contains a transparent window that enables the passage of the pinpoint beam of excitation light there through. The output end 210 of the illumination output device 207 can be positioned under one or more selected wells 231 of the array in order to trans-illuminate the specimen contained in the well.

Referring back to FIG. 11, another alternative embodiment of the trans-illumination device 206 is shown having a lens system 232 at the distal end of the second light transmission unit 216 that focuses the excitation light onto a movable optical element 233 that redirects the light toward the specimen 145 supported atop the window portion of the specimen stage. In this embodiment, the optical element 233 is preferably provided by a computer-controlled galvanometer having a reflective surface 235. Through precision control of the orientation of the reflective surface 235, via a control system, the reflected excitation light can be directed at strategic locations of the surface of the supported specimen 145 for trans-illumination thereof. While the reflective surface 235 of the optical element 233 is illustrated as substantially planar, it will be appreciated that the surface 235 may be convex or the like to facilitate focusing the light.

In yet another alternative embodiment, FIG. 12 illustrates a trans-illumination device 206 having a plurality of light emitting ends 236 spaced-apart about the transverse cross-sectional dimension of the window portion 213. More preferably, the light emitting ends 236 are provided the distal ends of one or more fiber optic strands 237 aligned in an array. By controlling the output of the excitation light to a selected strand or strands, via a fiber optic switching system 238 strategic regions of the specimen 145 can be trans-illuminated.

In one specific configuration, both the trans-illumination device 206 and the epi-illumination device 203 of the second illumination assembly 202 are illuminated by remote light sources. Since trans-illumination and epi-illumination devices are separate illumination procedures and are not to be performed simultaneously, a single remote light source 37 can be applied as opposed to requiring an independent light source for each device, as shown in the illumination systems 200 of FIGS. 10-12. Accordingly, as shown generally in FIGS. 17-22, an optical light switch 240 is positioned between the remote excitation light source 37 and the trans-illumination device 206 and the epi-illumination device 203 to selectively direct the passage of the excitation light. Briefly, the optical light switch 240 is selectively movable between a first position (FIGS. 17, 19, 20 and 22), directing the outputted excitation light to one of the epi-illumination device and the trans-illumination device, and a second position (FIGS. 18 and 21), directing the outputted excitation light to the other of the trans-illumination device and the epi-illumination device.

Figure 17:
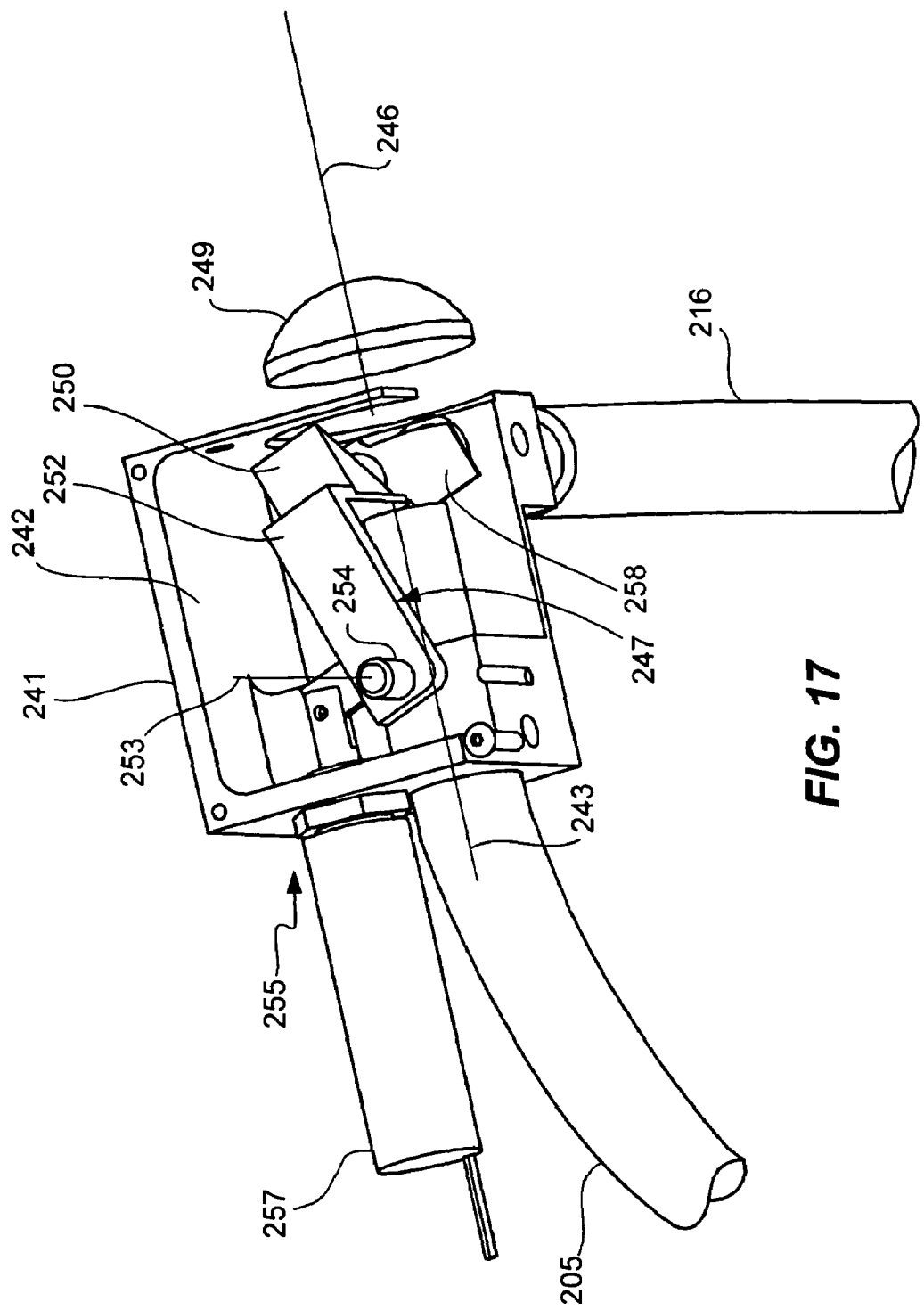
FIG. 17 is an enlarged top perspective view, partially broken away, of a switch element for the dual illumination system of FIG. 10, shown in a first position.
Figure 18:
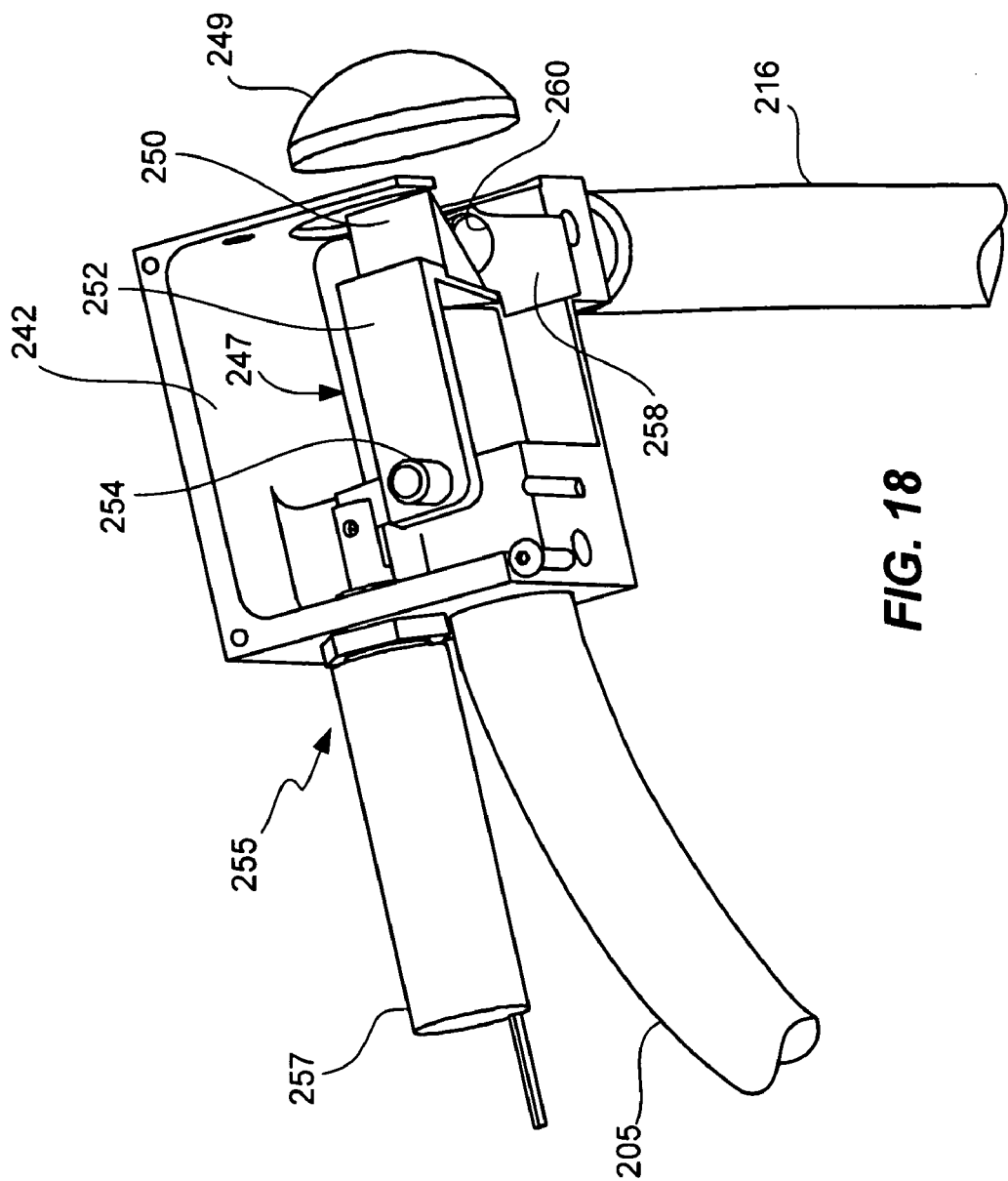
FIG. 18 is an enlarged top perspective view, partially broken away, of the switch element of FIG. 17, shown in a second position.
Figure 19:
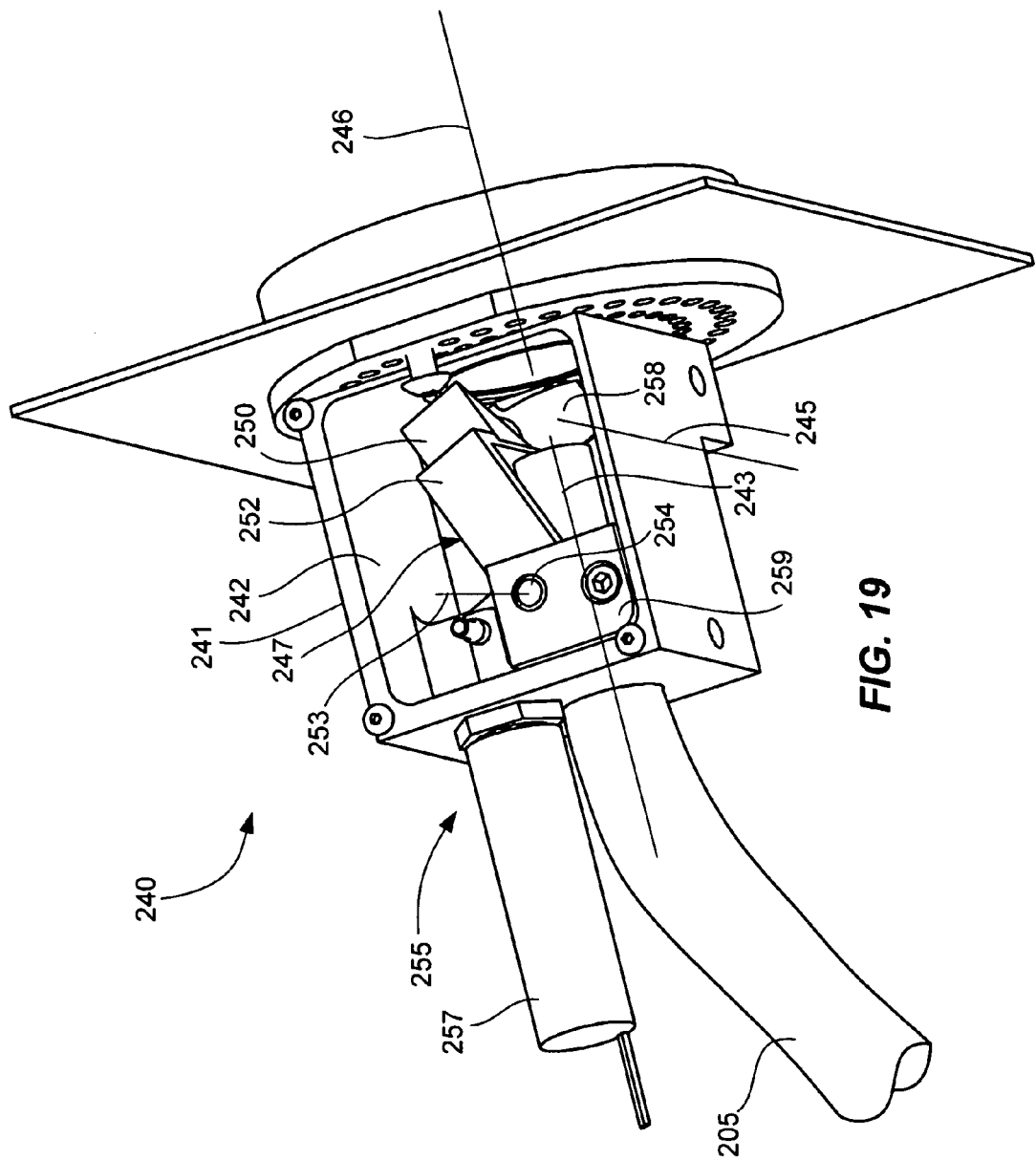
FIG. 19 is a top perspective view, partially broken away, of the switch element of FIG. 17, shown in a first position.
Figure 20:
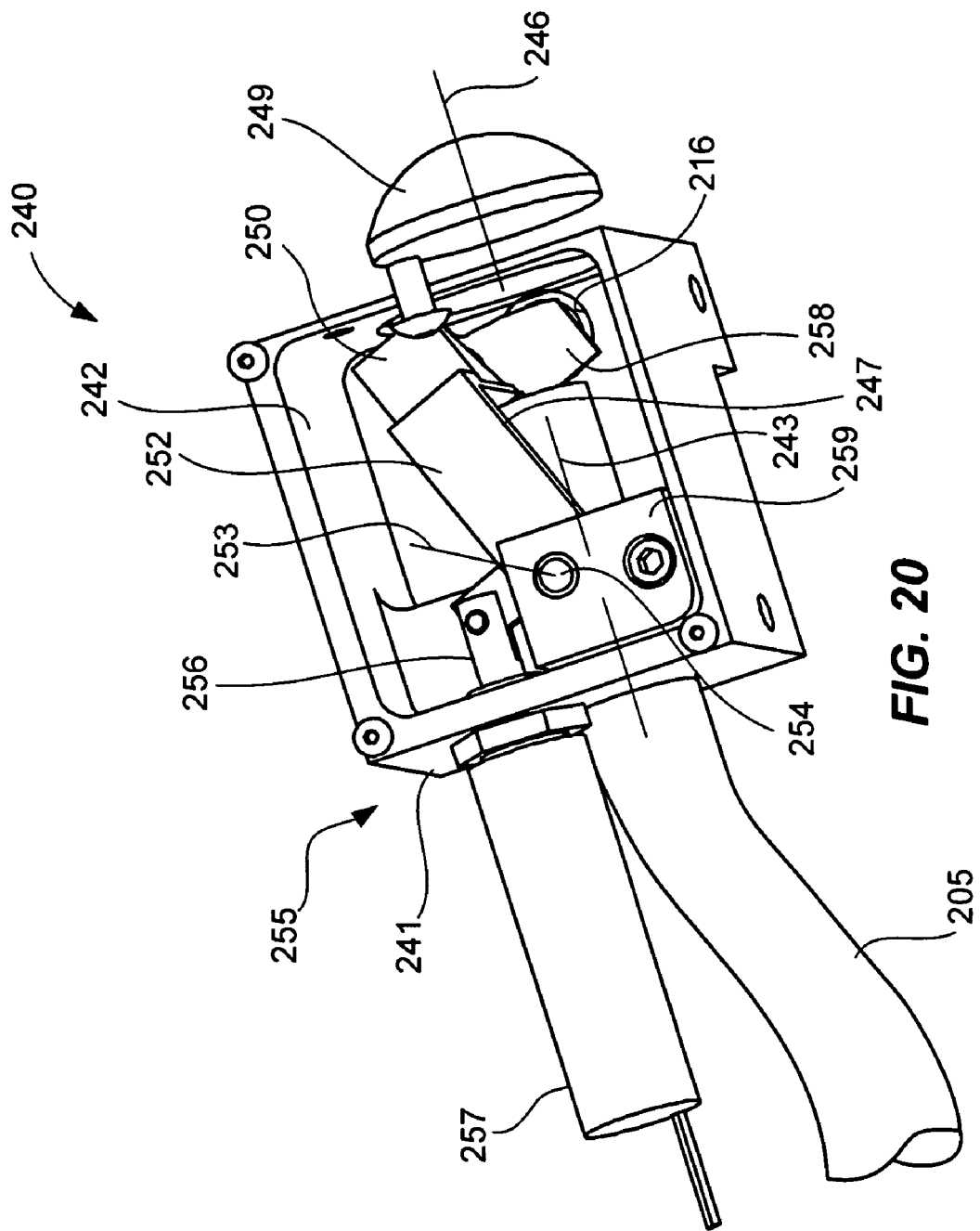
FIG. 20 is a top perspective view, partially broken away, of the switch element of FIG. 17, and illustrating a lens of a third light transmission unit
Figure 21:
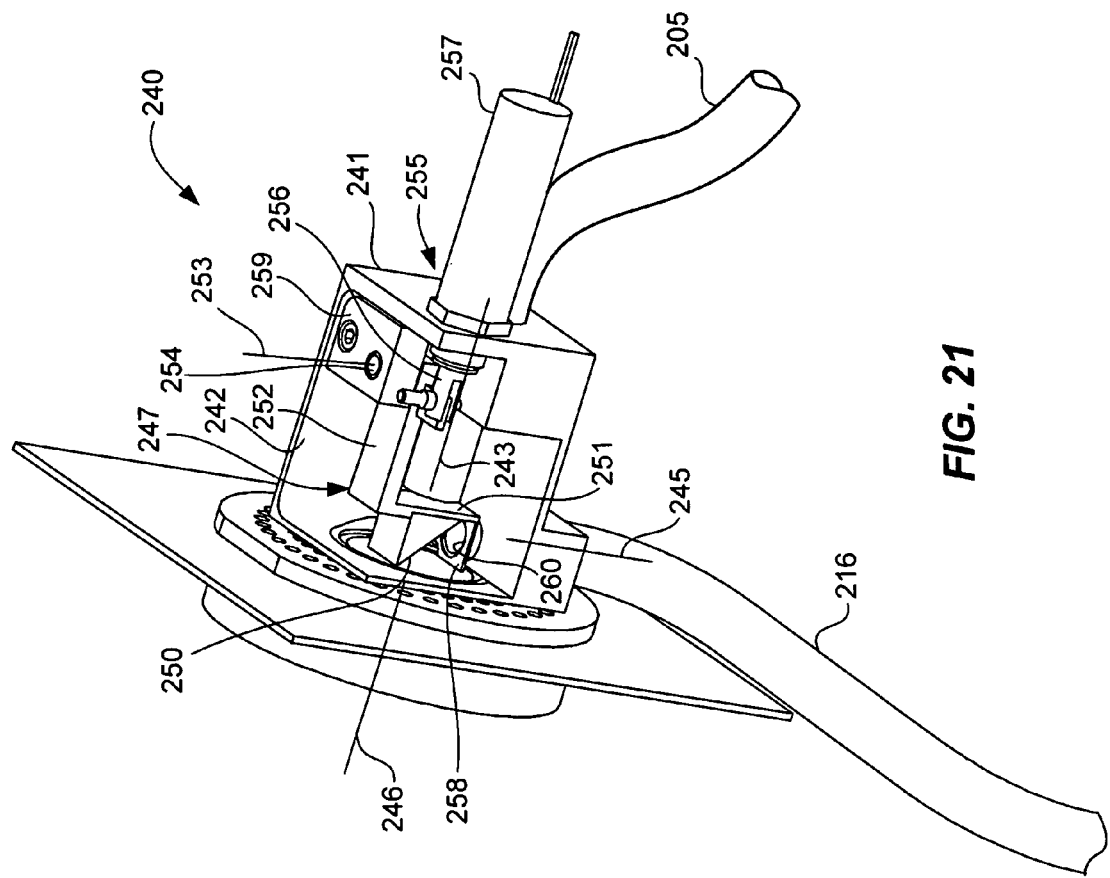
FIG. 21 is a side perspective view, partially broken away, of the switch element of FIG. 17, shown in a second position.
Figure 22:
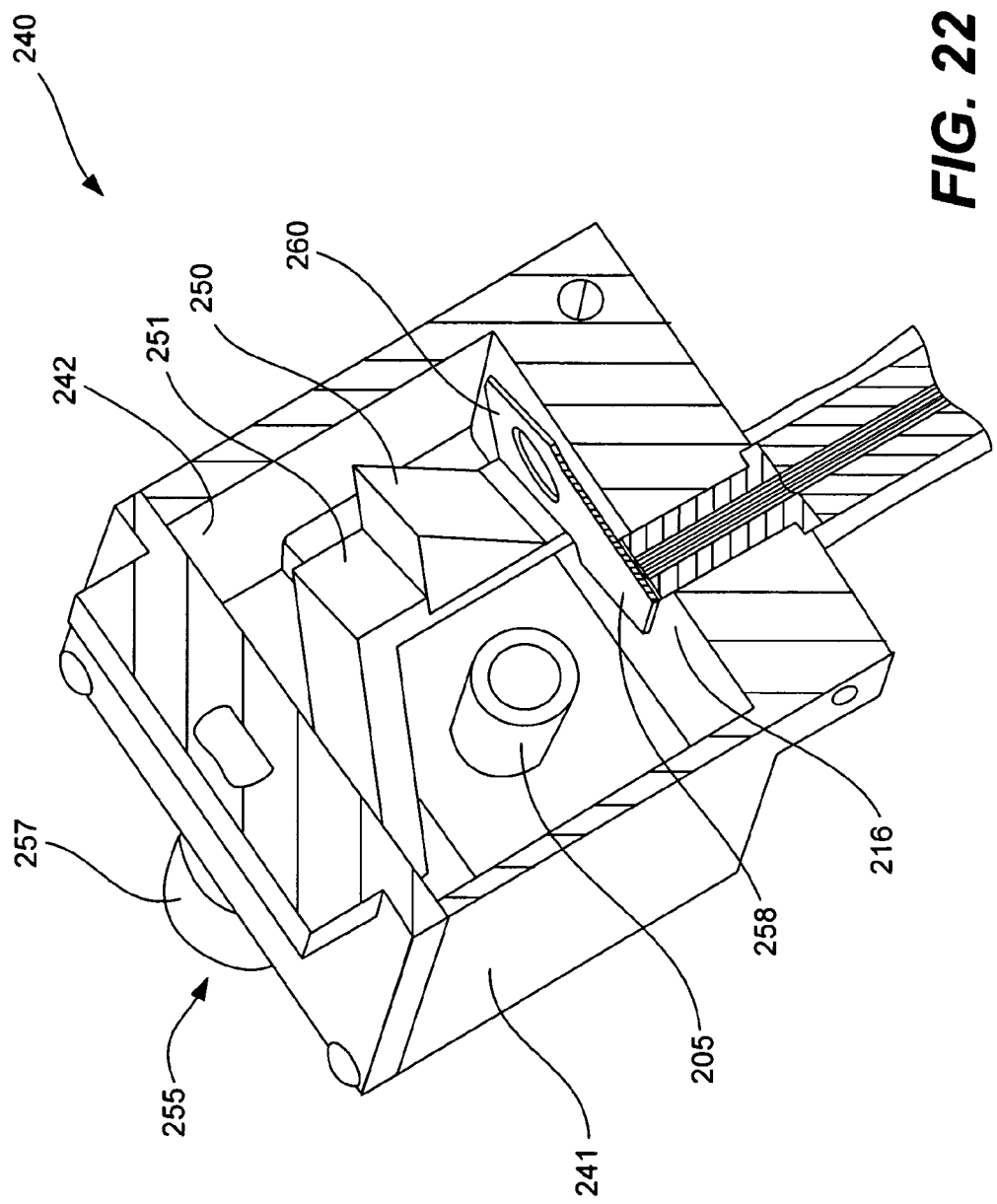
FIG. 22 is a front perspective view, partially broken away, of the switch element of FIG. 17, shown in a first position.

The light switch 240 includes a support housing 241 defining an enclosed interior cavity 242 upon which the epi-illumination device 203, the trans-illumination device 206, and the remote excitation light source 37 optically communicate. The housing 241 includes a first light path 243 into the cavity 242 that is in optical communication with the epi-illumination device 203, a second light path 245 into the cavity, in optical communication with the trans-illumination device 206, and a third light path 246 into the cavity in optical communication with the excitation light source 37. FIGS. 17, 18 and 21 best illustrate that the light switch 240 includes a switch element 247 that is selectively movable between the first position and the second position. In one configuration, briefly, the switch element 247 permits the passage of the excitation light across the interior cavity 242 from the third light path 246 to the first light path 243, in the first position, while manipulating the direction of excitation light across the interior cavity 242 from the third light path 246 to the second light path 245, in the second position. It will of course be appreciated that the light transmission units coupled to the respective light paths can be easily switched without departing from the true spirit and nature of the present invention.

In the embodiments illustrated, a proximal end of the first light transmission unit 205 communicates with the interior cavity 242 of the housing 241 along the first light path, while a proximal end of the second light transmission unit 216 communicates with the interior cavity 242 along the second light path. Further, the proximal ends of the light transmission units will often essentially be the proximal ends of the respective bundle of fiber optic strands.

Moreover, the remote light source 37 is in communication with the housing via a third light transmission unit or the like. In one configuration, a distal end of the third light transmission unit may terminate directly into the interior cavity of the housing, while a proximal end thereof is in communication with the excitation light source. In another arrangement, a lens device 249 or the like is positioned in the interior cavity 242 of the housing and aligned with the third light path 246. Hence, as the excitation light is emitted from the distal end of the third light transmission unit 248, it passes through the lens device that focuses the excitation light across the interior cavity 242. In still another embodiment, a filter wheel assembly 47 or the like can be positioned "in-line" with the third light transmission unit 248 between the light source 37 and the light switch 240. Hence, the light is filtered prior to entering the switch housing 241. Alternatively, of course, separate filtering of the excitation light can be performed downstream from the switch device.

Preferably, the filter wheel assembly is identical to the filter wheel assembly 47 shown in the embodiments of FIGS. 1-3. These assemblies include a plurality of optical filters contained on a wheel that can be selectably moved into the third light path of the excitation light.

Referring back to FIGS. 17 and 20, in one specific embodiment, the third light path 246 (i.e., in optical communication with the light source) is in substantial optical alignment with the either of the first light path (i.e., in optical communication with the epi-illumination device 203) or the second light path (i.e., in optical communication with the trans-illumination device 206). Briefly, it will be appreciated that while either the second light path or the first light path may be optically aligned with the third light path, heretofore, the first light path of the first transmission unit will be described as optically aligned with the third light path for clarity of description. It will further be apparent that neither the first light path 243 nor the second light path 245 need be in optical alignment with the third light path 246. In these configurations, the movable switch element 247 can be shaped to direct the emission of excitation light from the third light path to either the first light path or the second light path.

More preferably, however, the optical alignment between the first light path 243 and the third light path 246 is a substantially linear, co-axial alignment. As best viewed in FIG. 17, the first light path 243 is directly across from the third light path 246 in the housing interior cavity 242. Accordingly, to permit passage of the excitation light from the distal end of the third light path 246, across the housing interior cavity 242, to the proximal end of the first light transmission unit 205, the movable switch element 247, in the first position, is positioned out of the optical path of the excitation light transmitted from the third light path distal end. Hence, the excitation light outputted from the distal end of the third light path 246 passes unobstructed across the housing interior cavity 242 and directly into the proximal end of the bundle of fiber optic strands (i.e., the first light transmission unit 205) along the first light path 243.

In contrast, while the second light path 245 is preferably oriented and contained in substantially the same plane as that of the first light path 243 and the third light path 246 (although it need not be), it is positioned in a non-linear orientation relative to the third light path 246. By angling the second light path 245 relative to the third light path 246, the excitation light exiting the distal end of the third light path will not be directed into the proximal end of the second light transmission unit 216 when the movable switch element 247 is disposed in the first position.

More preferably, the second light path 245 is oriented substantially perpendicular to both the first light path 243 and the third light path 246, as shown in FIGS. 17, 18 and 221. While the second light path 245 can be off-set from the third light path 246 at nearly any angle between about 20° to about 60° from the optical axis of the third light path, about a 90° off-set is preferred due to the ease of optical manipulation of the excitation light in the direction of the second light path 245.

In the second position (FIGS. 19 and 21), thus, the movable switch element 247 is configured and oriented to direct the excitation light outputted from the third transmission unit 248 along the third light path 246 and into the proximal end of the second light transmission unit 216. In the embodiment shown in FIGS. 19 and 21, the excitation light is redirected about 90° toward the second light path 245 of the proximal end of the second light transmission unit 216. Preferably, the switch element includes a reflective surface 250 strategically oriented to reflect the outputted excitation light toward the second transmission unit. This reflective surface 250 is preferably mounted to a support flange portion 251 of the switch element 247 at about a 45° angle (since in this embodiment the second light path 245 is off-set about 90° from the third light path 246). Further, the surface of the reflective element is substantially planar, although not need be depending upon the desired reflection characteristics. Accordingly, in the second position, not only is the support flange portion 251 of the switch element 247 obstructively moved between the distal end of the third light transmission unit 248 and the proximal end of the first light transmission unit 205, but also strategically positions the reflective surface 250 to reflect the excitation light into the proximal end of the second light transmission unit 216.

To control the movement of the flange portion 251, the switch element 247 includes a support arm portion 252 containing an upstanding pivot post 254 that is pivotally coupled to a support bracket 259, which in turn is affixed to the housing 241. This pivot post 254 enables the switch element 247 to pivot about an axis 253 between the first position and the second position. A drive mechanism 255 is coupled to the support arm portion 252 for operation of the switch element 247. In one configuration, the drive mechanism 255 includes a drive rod 256 having one end pivotally mounted to the arm portion 252, and an opposite end mounted to a solenoid device 257 or the like. The solenoid device is then conventionally operated through a control unit or circuitry, reciprocating the drive rod, which in turn rotates the switch element 247 about the axis 253 between the first and second positions.

In accordance with one specific embodiment of the present invention, the switch element 247 includes a cover unit 258 that is positioned over the proximal end of the second light transmission unit 216 when the switch element 247 is in the first position. This functions to prevent substantially all the diffused or scattered excitation light in the housing interior cavity 242 from entering the proximal end of the second light transmission unit 216 where it would be emitted from the trans-illumination device 206. As best viewed in FIGS. 17, 19 and 20, this cover unit 258 may be a simple plate extension mounted to an end of the support flange portion 251. When the switch element 247 is moved to the first position, the cover unit 258 is moved over the proximal end of the second light transmission unit 216.

In contrast, when the switch element 247 is moved to the second position, the cover unit 258 is either moved out of the second light path 245 (i.e., from in front to the proximal end of the second light transmission unit 216) or enable entrance of excitation light into the second light transmission unit 216. In this particular design, the cover unit 258 includes an aperture 260 extending through the cover unit 258 that permits the passage of the excitation light after being reflected off of the reflective element. This aperture is sized diametrically at least as large as the proximal end of the second light transmission unit 216 to allow the passage of the light. This aperture 260 is oriented such that when the switch element is in the second position, the aperture 260 is substantially co-axially aligned with that of the second transmission unit proximal end, but when in the first position, the aperture will not permit the passage of light through to the second transmission unit.

Although only a few embodiments of the present inventions have been described in detail, it should be understood that the present inventions might be embodied in many other specific forms without departing from the spirit or scope of the inventions.

What is claimed is:

1. A dual illumination system for use with an imaging apparatus, said imaging apparatus defining a light-tight imaging compartment with an interior wall having a view port extending into said imaging compartment to enable data acquisition of a specimen contained in said imaging compartment, said dual illumination system comprising:

a first illumination assembly configured to direct structured light onto a first side of said specimen to enable structured light imaging and surface topography measurements thereof; and a second illumination assembly directing excitation light at said specimen wherein diffused fluorescent light emanates from a surface thereof for receipt through said view port to acquire fluorescence data of said specimen.

2. The dual illumination system as defined by claim 1, wherein
said second illumination assembly includes one of a trans-illumination device and an epi-illumination device.

3. The dual illumination system as defined by claim 2, wherein
    said second illumination assembly includes the other of the epi-illumination device and the trans-illumination device,
    said trans-illumination device being configured to direct light into a first surface of said specimen wherein the diffused light exits a second surface thereof for receipt through said of the diffused light from said view port, and
    said epi-illumination device being configured direct light onto a third surface of said specimen wherein the diffused light exits said third surface thereof for receipt through said view port.

4. The dual illumination system as defined by claim 3, wherein
    said trans-illumination device being configured to direct light into a bottom surface of said specimen wherein the diffused light exits a topside surface thereof for receipt through said of the diffused light from said view port, and
    said epi-illumination device being configured direct light onto the topside surface of said specimen wherein the diffused light exits said topside surface thereof for receipt through said view port.

5. The dual illumination system as defined by claim 4, wherein
    said epi-illumination device includes a first light transmission unit having a proximal end thereof in optical communication with an excitation light source and a distal end thereof terminating proximate said view port, and
    said trans-illumination device includes a second light transmission unit having a respective proximal end thereof in optical communication with said excitation light source and a respective distal end thereof configured to direct said light into the bottom side surface of said specimen.

6. The dual illumination system as defined by claim 5, further including:
    a specimen support surface positioned in said imaging compartment and defining a window portion enabling the passage of light there through; and
    the distal end of said second light transmission unit being configured to emit said light in a beam toward said window portion.

7. The dual illumination system as defined by claim 6, wherein
    said window portion of said specimen support surface being selectively sized and dimensioned such that the specimen, when supported atop the support surface, can be positioned and seated over said window portion in a manner forming a light-tight seal substantially there between.

8. The dual illumination system as defined by claim 6, wherein
    said trans-illumination device includes an illumination output device cooperating with the distal end of second light transmission unit to emit a pinpoint beam of said light toward said window portion.

9. The dual illumination system as defined by claim 8, wherein
    said trans-illumination device includes a translation mechanism supporting said illumination output device to selectively position the pinpoint beam of light at one of a plurality of positions adjacent said window portion.

10. The dual illumination system as defined by claim 5, wherein
    said first and second light transmission unit include a bundle of fiber optic strands.

11. The dual illumination system as defined by claim 5, wherein
    said second illumination assembly includes an optical light switch positioned between the excitation light source and the proximal ends of the respective first and second light transmission units for selective directing the excitation light to one of the epi-illumination device and the trans-illumination device.

12. The dual illumination system as defined by claim 11, further including:
    an excitation interference filter positioned in between the excitation light source and the light switch to filter the light passing therethrough.

13. The dual illumination system as defined by claim 11, wherein
    said light switch includes a housing defining a cavity and having a first light path into said cavity in optical communication with said epi-illumination device, a second light path into said cavity in optical communication with said trans-illumination device, a third light path into said cavity in optical communication with said light source, and a switch element selectively movable between the first position and the second position.

14. The dual illumination system as defined by claim 13, wherein
    said first light transmission unit includes a proximal end disposed in said cavity along the first light path, and said second light transmission unit includes a proximal end disposed in said cavity along the second light path, one of the first light path and the second light path being in substantially linear, co-axial alignment with a the third light path, and the other of the second light path and the first light path being in non-linear alignment with the third light path, and
    said switch element, in the first position, being positioned out of the optical path of the excitation light transmitted in substantially linear, co-axial alignment from the third light path distal end to one of the first light path and the second light path therewith, and in the second position, being positioned in the optical path of the excitation light transmitted from the third light path distal end for optical redirection to along the other of the second light path and the first light path.

15. The dual illumination system as defined by claim 14, wherein
    said switch element includes reflective element configured to reflect the excitation light from the third light path to the other of the second light path and the first light path, in the second position.

16. The dual illumination system as defined by claim 15, wherein
    said epi-illumination device further includes a first light transmission unit having a proximal end thereof in optical communication with the housing cavity along the first light path, and
    said trans-illumination device includes a second light transmission unit having a respective proximal end thereof in optical communication with the housing cavity along said second light path, and a respective distal end thereof configured to direct said light into a bottom side surface of said specimen.

17. The dual illumination system as defined by claim 15, wherein
    said switch element is pivotally mounted in said cavity between the first position and the second position.

18. The dual illumination system as defined by claim 17, wherein
said light switch further includes a drive rod having one end pivotally mounted to the switch element, and another end associated with a drive mechanism.

19. The dual illumination system as defined by claim 14, wherein
said switch element includes a cover device configured to cooperate with the one of the proximal end of the first light transmission unit and the proximal end of the second light transmission unit, in the second position, to substantially block the passage of light into the other of the proximal end of the second light transmission unit and the proximal end of the first light transmission unit from the housing cavity.

20. The dual illumination system as defined by claim 5, wherein
said excitation light source is a tungsten halogen lamp.

21. The dual illumination system as defined by claim 3, wherein
said epi-illumination device includes an illumination output end disposed directly into the imaging compartment, and positioned proximate to and peripherally encircling said view port such that said specimen is illuminated in a substantially uniform manner.

22. The dual illumination system as defined by claim 21, wherein
said epi-illumination device includes a frame substantially peripherally encircling said view port, and adapted to support the output end of said illumination device.

23. The dual illumination system as defined by claim 22, wherein
said epi-illumination device includes a bundle of fiber optic strands extending into said imaging compartment at said output end, having distal ends thereof terminating at the frame to emit a conical directional beam of light onto said specimen, said distal ends of said fiber optic strands being sufficiently spaced peripherally about the view port such that the plurality of directional beams collectively illuminate the specimen in the substantially uniform manner.

24. The dual illumination system as defined by claim 1, wherein
said first illumination assembly includes employs a laser galvanometer scanning device.

25. The dual illumination system as defined in claim 24, wherein
said laser galvanometer is programmed through computer control to project a structured light pattern onto the specimen.

26. The dual illumination system as defined in claim 1, wherein
said first illumination system employs a projection device, consisting of Ronchi ruling that is illuminated by an LED and optically projected onto the specimen.

27. A method for performing 3D diffuse fluorescence tomography reconstruction, using a single imaging apparatus, for a specimen disposed in a light-tight imaging compartment of the imaging apparatus, said method comprising:
applying structured light to a surface of said specimen in the imaging compartment to determine the 3D surface topography thereof;
applying fluorescence excitation light to said specimen to acquire fluorescence imaging data thereof; and
calculating the 3D diffuse fluorescence tomography reconstruction using the 3D surface topography data and the fluorescence image data, acquired from the single imaging apparatus.

28. The method according to claim 27, wherein
said applying fluorescence excitation light is performed by using a trans-illumination excitation light.

29. The method of claim 28, wherein
said using a trans-illumination light source includes moving the trans-illumination light source to a plurality of positions relative to the specimen in the imaging compartment.

30. The method of claim 27 wherein
said applying fluorescence excitation light is performed by using an epi-illumination light source.

31. The method of claim 28, wherein
said applying fluorescence excitation light is further performed by using a trans-illumination excitation light source to acquire trans-illumination fluorescence imaging data, and
said calculating the 3D diffuse fluorescence tomography reconstruction includes using epi-illumination fluorescence imaging data and the trans-illumination fluorescence imaging data in a 3D diffuse tomographic algorithm.

32. The method of claim 31 wherein,
said applying fluorescence excitation light includes acquiring one of the epi-illumination fluorescence imaging data and the trans-illumination fluorescence imaging data at a plurality of excitation or emission filter wavelengths.

* * * * *